US010983125B2

United States Patent
Kim et al.

(10) Patent No.: US 10,983,125 B2
(45) Date of Patent: Apr. 20, 2021

(54) MARKER FOR DETECTING HIGHLY PATHOGENIC INFLUENZA VIRUS AND USE THEREOF

(71) Applicant: DANDI BIOSCIENCE INC, Seoul (KR)

(72) Inventors: Kyun-Hwan Kim, Seoul (KR); Eun Sook Park, Seoul (KR); Yeong-Min Park, Seoul (KR); Baik Lin Seong, Seoul (KR); Young Ho Byun, Seoul (KR); Hye Min Lee, Seoul (KR)

(73) Assignee: Dandi Bioscience Inc, Seoul (KR)

( * ) Notice: Subject to any disclaimer, the term of this patent is extended or adjusted under 35 U.S.C. 154(b) by 0 days.

(21) Appl. No.: 16/464,866

(22) PCT Filed: Nov. 29, 2017

(86) PCT No.: PCT/KR2017/013843
§ 371 (c)(1),
(2) Date: May 29, 2019

(87) PCT Pub. No.: WO2018/101747
PCT Pub. Date: Jun. 7, 2018

(65) Prior Publication Data
US 2020/0132688 A1    Apr. 30, 2020

(30) Foreign Application Priority Data

Nov. 29, 2016 (KR) .................. 10-2016-0159926

(51) Int. Cl.
   *G01N 33/569*   (2006.01)
   *C07K 14/005*   (2006.01)
   *G01N 33/50*    (2006.01)

(52) U.S. Cl.
   CPC ..... *G01N 33/56983* (2013.01); *C07K 14/005* (2013.01); *G01N 33/505* (2013.01); *C07K 2319/00* (2013.01); *C12N 2760/16122* (2013.01)

(58) Field of Classification Search
   None
   See application file for complete search history.

(56) References Cited

U.S. PATENT DOCUMENTS

| 10,124,059 | B2 * | 11/2018 | Lange ............... A61K 39/145 |
| 2012/0282593 | A1 | 11/2012 | McCullers et al. |
| 2013/0137083 | A1 | 5/2013 | Khurana et al. |

OTHER PUBLICATIONS

Raman et al., DDX3 interacts with influenza A virus NS1 and NP proteins and exerts antiviral function through regulation of stress granule formation. J Virol 90:3661-3675 (Year: 2016).*
Varga et al., Virulence 2:6, 542-546; Nov./Dec. 2011.*
Alymova et al., 'A novel cytotoxic sequence contibutes to influenza a viral protein PB1-F2 pathogenicity and predisposition to secondary bacterial infection' Journal of Virology, 2014, vol. 88, No. 1, pp. 503-515.
Conenello et al., 'A single mutation in the PB1-F2 of H5N1 (HK/97) and 1918 influenza A viruses contributes to increased virulence' PLoS Pathogens, 2007, vol. 3, Issue 10, Article No. e141, pp. 1414-1421.
Conenello et al., 'A single N66S mutation in the PB1-F2 protein of influenza A virus increases virulence by inhibiting the early interferon response in vivo' Journal of Virology, 2011, vol. 85, No. 2, pp. 652-662.
Raman et al., 'DDX3 interacts with influenza A virus NS1 and NP proteins and exerts antiviral function through regulation of stress granule formation' Journal of Virology, Apr. 2016, vol. 90, No. 7, pp. 3661-3675.

* cited by examiner

*Primary Examiner* — Shanon A. Foley
*Assistant Examiner* — Myron G Hill
(74) *Attorney, Agent, or Firm* — Vorys, Sater, Seymour & Pease LLP; Mih Suhn Koh

(57) ABSTRACT

Provided are a marker for detecting a highly pathogenic influenza virus including a protein mutant prepared by substituting the amino acids 68 and 69 of a PB1-F2 protein, a composition for detecting a highly pathogenic virus including an agent for measuring the protein mutant, and a detection kit including the same, a method for detecting a highly pathogenic virus including measuring the protein mutant, an antiviral composition against influenza A virus including an inhibitor of binding between a PB1-F2 protein in which the amino acids 68 and 69 are substituted and DDX3, and a method for screening an antiviral substance against influenza A virus.

8 Claims, 33 Drawing Sheets
Specification includes a Sequence Listing.

FIG. 2B

| | | | | |
|---|---|---|---|---|
| HA-PB1-F2(PR8) | + | − | + | − |
| HA-PB1-F2(1918) | − | + | − | + |
| Flag-Ubi | − | − | + | + |

IP: HA
IB: Flag

Ubiquitinated PB1-F2

Input

Flag

PB1-F2

β-actin

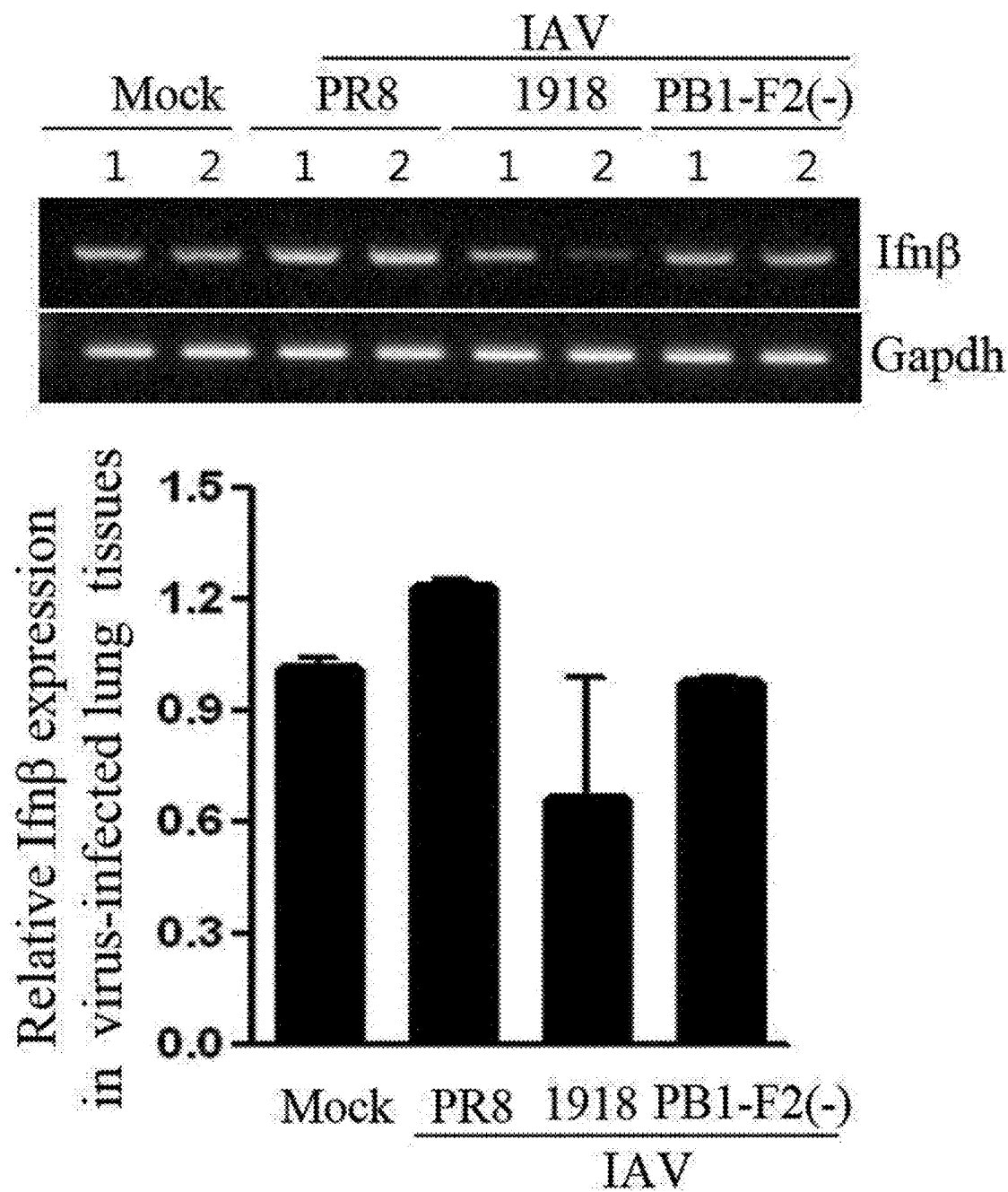

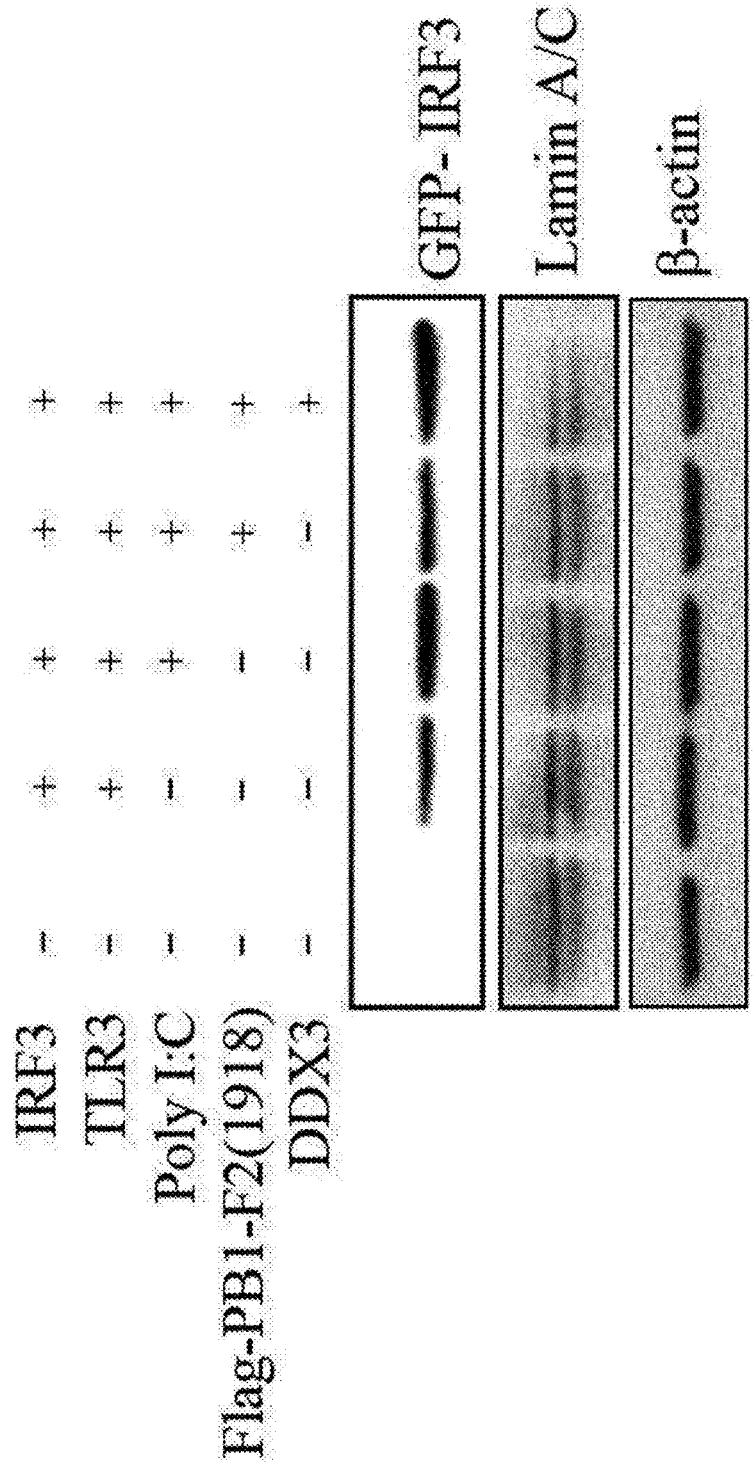

FIG. 9A

IAV; 1918 PB1-F2 (1×10⁵ pfu)
Protein; LysRS-DDX3 (1ug)

0h

Viral lung titer & IFNβ

2d

Measurement of survival rate

14d

MARKER FOR DETECTING HIGHLY PATHOGENIC INFLUENZA VIRUS AND USE THEREOF

STATEMENT REGARDING GOVERNMENT RIGHTS

The present invention was undertaken with the support of 1) Control of cytokine storm based on the mechanism of pathogenicity of influenza PB1-F2 derived from 1918 spanish strain No. A103001 grant funded by the Ministry of Health & Welfare and 2) Needle-free Vaccine Delivery Development No. HI13C0826 grant funded by the Ministry of Health & Welfare.

CROSS-REFERENCE TO RELATED APPLICATION

This application is a 371 of PCT/KR2017/013843, filed Nov. 29, 2017, which claims the benefit of priority from Korean Patent Application No. 10-2016-0159926, filed Nov. 29, 2016, the contents of each of which are incorporated herein by reference in its entirety.

SEQUENCE LISTING

The Sequence Listing submitted in text format (.txt) filed on Oct. 1, 2019, named "SequenceListing.txt", created on Oct. 1, 2019 (12.6 KB), is incorporated herein by reference.

Technical Field

The present invention relates to a marker for detecting a highly pathogenic influenza virus and a use thereof, and more particularly, to a marker for detecting a highly pathogenic influenza virus, which includes a protein mutant prepared by substituting the amino acids 68 and 69 of a PB1-F2 protein, a composition for detecting a highly pathogenic virus, which includes an agent for measuring the protein mutant and a detection kit including the same, a method for detecting a highly pathogenic virus, which includes measuring the protein mutant, an antiviral composition against influenza A virus, which includes an inhibitor of binding between a PB1-F2 protein in which the amino acids 68 and 69 are substituted and Dead box protein 3 (DDX3) as an active ingredient, and a method for screening an antiviral substance against influenza A virus.

Background Art

Influenza A virus (IAV) is a pathogen capable of infecting both humans and animals, and a virus which caused Spanish flu resulting in the deaths of 50 million people in 1918. PB1-F2 is a non-structural protein of an influenza virus encoded by a part from the +1 open reading frame to a PB1 gene. Until now, through various studies, PB1-F2 has been reported to have various functions including apoptosis induction and inhibition of innate immunity, and has been known as a significant factor exhibiting virality associated with pathogenicity in a very highly pathogenic influenza virus. It has been reported that this protein contributes to the pathogenesis of influenza by inhibiting production of cytokines, increasing immunopathology of secondary bacterial infection, and delaying viral clearance during the infection of IAV in mouse models.

In the first defense mechanism against influenza virus infection, type I interferon (type I IFN) is a significant factor for antiviral immunity of a host, and a regulator for adaptive immunity. When a host is infected with a virus such as an influenza virus or another pathogen, three types of main proteins known as pattern-recognition receptors (PRRs) inducing innate immunity recognize pathogen-associated molecular patterns (PAMPs) of pathogens. Such PRRs include toll-like receptors (TLRs), retinoic acid inducible gene-I (RIG-I)-like receptors (RLRs), and nucleotide-binding domain-leucine-rich repeat-containing molecules (NLRs), and when a host is infected with an influenza virus, RIG-I serves as main sensor of viral RNA to induce the production of type I IFN. In such a pathway, formation of a complex of DDX3 and a different phosphokinase has been known to be essential for induction of the production of type I IFN.

Although an IFN system has strong antiviral activity, influenza viruses have also been evolved to attenuate an IFN response for replication and proliferation thereof in a host. For example, it was reported that an NS1 protein of a highly pathogenic virus such as the H5N1 avian influenza virus has a strong inhibitory effect on type I IFN, and rapid collection of neutrophils, a serious lung damage, and rapid secretion of inflammatory cytokines are induced in Ifnar1−/−mice (*Proc Natl Acad Sci USA* 2002; 99:10736-10741).

In the present invention, in order to investigate the influence of a PB1-F2 protein of a highly pathogenic 1918 strain on the pathogenic mechanism of IAV infection, the correlation between viral virulence and the PB1-F2 protein was examined, and a molecular mechanism related to inhibition of a type I IFN response was to be identified.

DISCLOSURE

Technical Problem

As a result of the investigation of the influence of a PB1-F2 protein in a highly pathogenic 1918 strain of IAV on virulence and the correlation therebetween, the inventors first identified the correlation between the 1918 PB1-F2 protein and high pathogenicity of the virus and the molecular mechanism thereof by confirming that low stability of the virus is mediated by the amino acids 68 and 69 on the sequence of the PB1-F2 protein of the 1918 strain, and virulence of the virus is increased by inhibiting the expression of INFβ inducing an antiviral response through binding to intracellular DDX3, and based on this finding, the present invention was completed.

Therefore, the present invention is directed to providing a marker composition for detecting a highly pathogenic influenza virus, which includes a protein mutant prepared by substituting the amino acids 68 and 69 of a PB1-F2 protein consisting of an amino acid sequence of SEQ ID NO: 1.

In addition, the present invention is directed to providing a composition for detecting a highly pathogenic virus, which includes an agent for measuring the protein mutant, and a kit for detecting a highly pathogenic virus, which includes the composition.

In addition, the present invention is directed to providing a method for detecting a highly pathogenic virus, which includes measuring the protein mutant.

In addition, the present invention is directed to providing an antiviral composition against IAV, which includes an inhibitor of binding between DDX3 and a PB1-F2 protein as an active ingredient.

In addition, the present invention is directed to providing a method for screening an antiviral substance against IAV.

However, technical problems to be solved in the present invention are not limited to the above-described problems, and other problems which are not described herein will be fully understood by those of ordinary skill in the art from the following descriptions.

Technical Solution

To achieve the objects of the present invention, the present invention provides a marker composition for detecting a highly pathogenic influenza virus, which includes a protein mutant prepared by substituting the amino acids 68 and 69 of a PB1-F2 protein consisting of an amino acid sequence of SEQ ID NO: 1.

In addition, the present invention provides a composition for detecting a highly pathogenic virus, which includes an agent for measuring a protein mutant prepared by substituting the amino acids 68 and 69 of a PB1-F2 protein consisting of an amino acid sequence of SEQ ID NO: 1, and a detection kit including the same.

In addition, the present invention provides a method for detecting a highly pathogenic virus, which includes measuring a protein mutant prepared by substituting the amino acids 68 and 69 of a PB1-F2 protein consisting of an amino acid sequence of SEQ ID NO: 1.

In one exemplary embodiment of the present invention, the protein mutant may be prepared by substituting the amino acids 68 and 69 with threonine and proline, respectively.

In another exemplary embodiment of the present invention, the protein mutant may consist of an amino acid sequence of SEQ ID NO: 2.

In still another exemplary embodiment of the present invention, the virus may be an influenza virus.

In yet another exemplary embodiment of the present invention, the agent for measuring the protein mutant may be an antibody specifically binding to the protein.

In addition, the present invention provides an antiviral composition against IAV, which includes an inhibitor of binding between DDX3 and a PB1-F2 protein as an active ingredient, and the PB1-F2 protein may be prepared by substituting the amino acids 68 and 69 on the amino acid sequence of SEQ ID NO: 1.

In one exemplary embodiment of the present invention, the DDX3 may consist of an amino acid sequence of SEQ ID NO: 3.

In another exemplary embodiment of the present invention, the binding inhibitor may be any one selected from the group consisting of a nucleic acid, a compound, a microbial culture medium or extract, a natural substance extract, a peptide, a substrate analog, an aptamer, and an antibody.

In yet another exemplary embodiment of the present invention, the PB1-F2 protein may be prepared by substituting the amino acids 68 and 69 with threonine and proline, respectively.

In yet another exemplary embodiment of the present invention, the PB1-F2 protein may consist of an amino acid sequence of SEQ ID NO: 2.

In yet another exemplary embodiment of the present invention, the composition may increase the production of interferon beta (IFNβ) in cells.

In addition, the present invention may provide a method for screening an antiviral substance against IAV, which includes:

(a) in vitro treating cells with a candidate substance;
(b) measuring binding between DDX3 and a PB1-F2 protein in the cells; and (c) selecting a substance decreasing the binding between the DDX3 and the PB1-F2 protein as an antiviral substance against IAV, compared to a candidate substance untreated group, and the PB1-F2 protein may be prepared by substituting the amino acids 68 and 69 of an amino acid sequence of SEQ ID NO: 1.

In one exemplary embodiment of the present invention, the candidate substance may be selected from the group consisting of a nucleic acid, a compound, a microbial culture medium or extract, a natural substance extract, a peptide, a substrate analog, an aptamer, and an antibody.

In another exemplary embodiment of the present invention, the nucleic acid may be selected from the group consisting of siRNA, shRNA, microRNA, antisense RNA, an aptamer, a locked nucleic acid (LNA), a peptide nucleic acid (PNA), and a morpholino.

In still another exemplary embodiment of the present invention, step (b) is executed using a method selected from the group consisting of western blotting, immunoprecipitation, immunohistochemistry, and immunofluorescence.

In addition, the present invention provides a method for treating IAV, which includes administering an antiviral composition including an inhibitor of binding between DDX3 and a PB1-F2 protein as an active ingredient into a subject.

Moreover, the present invention provides a use of an antiviral composition for treating IAV, which includes an inhibitor of binding between DDX3 and a PB1-F2 protein as an active ingredient.

Advantageous Effects

From the pathogenic mechanism of IAV infection, the inventors first identified that low stability of the virus is mediated by the amino acids 68 and 69 on the sequence of a PB1-F2 protein of a 1918 strain using the highly pathogenic 1918 strain and a low-pathogenic PR8 strain, and virulence of the virus is increased by inhibiting expression of IFNβ inducing an antiviral response through binding to intracellular DDX3, a protein mutant prepared by substituting the amino acids 68 and 69 on the PB1-F2 protein sequence of an influenza virus can be used as a marker for detecting a highly pathogenic virus, and a highly pathogenic virus can be effectively detected by measuring the mutant.

In addition, the viral mechanism of the evasion of innate immunity by the PB1-F2 protein mutant, which was newly identified in the present invention, can provide new understanding for developing an antiviral agent, and the antiviral composition according to the present invention can be effectively used in development of an antiviral agent.

DESCRIPTION OF DRAWINGS

FIGS. 2a and 2b show that a 1918 PB1-F2 protein is degraded according to a proteasome-dependent pathway, where FIG. 2a shows the result of measuring PB1-F2 mRNA and protein expression levels through RT-PCR and western blotting after A549 cells are transfected with Flag-tagged PR8 or 1918 PB1-F2 expression plasmids and treated with MG132, a proteasome inhibitor, and FIG. 2b shows the result of ubiquitination analysis, representing that the PB1-F2 protein is degraded by a ubiquitin-proteasome system.

FIG. 3a illustrates various mutant plasmids of PR8 and 1918 PB1-F2, FIG. 3b shows the results of RT-PCR and western blotting for measuring PB1-F2 mRNA and protein expression levels after A549 cells are transfected with each of PB1-F2 chimeric mutants such as PR8-N+1918-C and 1918-N+PR8-C, FIG. 3c shows PB1-F2 mRNA and protein expression levels measured by the same method as used in FIG. 3b after cells are transfected with a c-terminal point mutant expression plasmid prepared by substituting some amino acids on the PR8 PB1-F2 sequence with those of 1918 PB1-F2, and FIG. 3d shows PB1-F2 mRNA and protein expression levels measured by the same method as used in FIG. 3b after PB1-F2 protein backbones of the PR8 and 1918 strains in which the amino acids 68 and 69 are substituted are cloned, and then cells are transfected with each type of plasmids.

FIG. 4a shows NF-κB luciferase activity and mRNA expression levels of pro-inflammatory cytokines (IL6, IL1β, and IL32) in cells transfected with PR8 and 1918 PB1-F2 expression plasmids, FIG. 4b shows the results of semi-quantitative PCR and real-time PCR for measuring IFNβ mRNA expression levels in A549 and U937 cells transfected with PR8 and 1918 PB1-F2 expression plasmids, FIG. 4c shows the result of luciferase reporter analysis for measuring a promoter activity of IFNβ in U937 cells, and FIG. 4d shows the results of RT-PCR and western blotting for measuring intracellular IFNβ mRNA and protein expression levels after A549 and U937 cells are infected with PR8 and 1918 strains of IAV at MOI 1.

FIG. 5a shows the results of semi-quantitative RT-PCR and western blotting for measuring IFNβ mRNA and protein expression levels depending on the treatment of a proteasome inhibitor such as MG132 in A549 and U937 cells transfected with PR8 and 1918 PB1-F2 expression plasmids, and FIG. 5b shows the results of semi-quantitative RT-PCR and western blotting for measuring IFNβ mRNA and protein expression levels after cells are transfected with a mutant expression plasmid prepared by substituting the amino acids 68 and 69 on a PR8 PB1-F2 sequence with those of 1918 PB1-F2.

FIGS. 6a to 6f show the influence of the amino acids 68 and 69 of 1918 PB1-F2 on pathogenicity of the 1918 strain of IAV, where FIGS. 6a and 6b show changes in body weight and survival rates of mice measured for 14 days after PR8 and 1918 strains of influenza virus were intranasally administered into the mice at $5 \times 10^2$ PFU and $1 \times 10^3$ PFU, respectively, FIG. 6c shows the body weights and survival rates after mice are infected with a mutant influenza virus prepared by substituting the amino acids 68 and 69 of the PR8 PB1-F2 protein with those of 1918 PB1-F2, and FIGS. 6d to 6f show the body weights and survival rates after mice are infected with the same mutant influenza virus as used in FIG. 6c at various contents ($6 \times 10^2$, $8 \times 10^2$, and $1 \times 10^3$ PFU).

FIGS. 7a to 7d show that IFNβ induction is inhibited by 1918 PB1-F2 in an IAV-infected model, where FIG. 7a shows the result of western blotting for measuring expression levels of viral proteins such as PB1-F2, nucleoprotein (NP), and hemagglutinin (HA) in mouse lung tissue two days after mice are infected with PR8, 1918, and PB1-F2-depleted 1918 (PB1-F2(−)) viruses at $5 \times \times 10^2$ PFU, FIG. 7b shows the result of a plaque assay for measuring the titer of each IAV using a lung tissue lysate of each group of mice of FIG. 7a, FIG. 7c shows the result of RT-PCR for measuring IFNβ mRNA expression levels using lung tissue of each group of mice of FIG. 7a, and FIG. 7d shows the result of ELISA for measuring IFNβ protein levels secreted from lungs of each group of mice of FIG. 7a.

FIGS. 8a to 8f show a mechanism of inhibiting IFNβ induction by binding between 1918 PB1-F2 and DDX3, where FIG. 8a shows proteins having a function associated with viral infection among proteins deduced to be interacted with 1918 PB1-F2, FIG. 8b shows the results of confirming binding between PB1-F2 (1918 strain) and a DDX3 protein under the condition of MG132 treatment after A549 cells are transfected with a DDX3 expression plasmid (HA-tagged DDX3) and a PB1-F2 expression plasmid (Flag-tagged PB1-F2) of a PR8 or 1918 strain and subjected to IP, or transfected with a mutant (I68T, L69P, or I68T/L69P) expression plasmid prepared by substituting the amino acids 68 and 69 of PR8 PB1-F2 with those of 1918 PB1-F2, FIG. 8c is the result of measuring expression levels of DDX3 proteins through western blotting after A549 cells are infected with PR8, 1918, and PR8-PB1-F2(−) viruses, FIG. 8d is the result of measuring expression levels of DDX3 proteins in lung tissue after mice are infected with IAV, FIG. 8e shows the result of checking nuclear translocation of IRF3 by 1918 PB1-F2, and FIG. 8f shows the result of analyzing changes in IFNβ mRNA expression after A549 cells are transfected with PR8, 1918 PB1-F2 expression plasmids, and a DDX3 expression plasmid.

FIGS. 9a to 9d show that pathogenicity of the 1918 PB1-F2 influenza virus is decreased due to treatment of recombinant DDX3 in an in vivo model, where FIG. 9a illustrates a process of an in vivo experiment, FIG. 9b shows the survival rates measured for two weeks after a recombinant DDX3 protein is administered to mouse models infected with 1918 IAV, FIG. 9c shows a 1918 IAV titer measured in lung tissue of the mouse model, and FIG. 9d shows the IFNβ mRNA expression levels in lung tissue of the mouse models.

MODE FOR INVENTION

Figure 1:
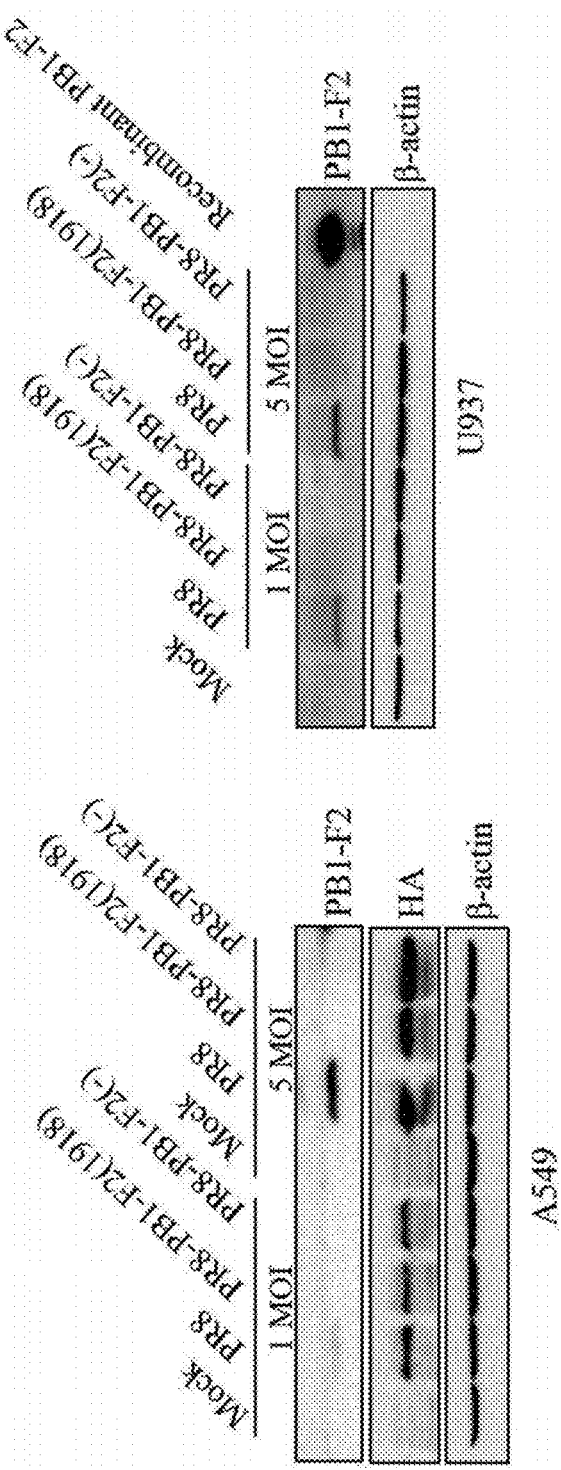
FIG. 1 shows that a PB1-F2 protein of the 1918 strain of IAV (hereinafter referred to as 1918 PB1-F2) has low stability, confirmed by measuring an expression level of the PB1-F2 protein through western blotting after A549 and U937 cells are infected with each of a PR8 strain (PR8), a PR8 strain of the virus whose amino acid sequence is changed with that of 1918 PB1-F2 (PR8-PB1-F2(1918)) and a PR8 strain of the virus from which a PB1-F2 protein is depleted (hereinafter referred to as PR8-PB1-F2(−)) at MOI 1 or 5 for 24 hours.

As a result of investigation of the influence of a PB1-F2 protein on virulence in a highly pathogenic 1918 strain of IAV and the correlation therebetween, the inventors confirmed that low stability of the virus is mediated by the amino acids 68 and 69 on the PB1-F2 protein sequence of the 1918 strain, and viral virulence is increased by inhibiting IFNβ expression inducing an antiviral response through the binding between the PB1-F2 protein and intracellular DDX3, and also confirmed that the IFNβ expression is restored by injecting a recombinant DDX3 protein into a mouse infected with 1918 PB1-F2 influenza virus, and the viral pathogenicity is decreased due to an increased survival rate. Therefore, the correlation between the 1918 PB1-F2 protein and the high pathogenicity of the virus and a molecular mechanism thereof were first identified, and based on these, the present invention was completed.

Accordingly, the present invention provides a marker composition for detecting a highly pathogenic influenza virus, which includes a protein mutant prepared by substituting the amino acids 68 and 69 of a PB1-F2 protein consisting of an amino acid sequence of SEQ ID NO: 1.

In the present invention, the PB1-F2 protein is preferably a non-structural protein of an influenza virus encoded by a part from the +1 open reading frame to a PB1 gene. The protein has been known to induce apoptosis by mediating the efflux of cytochrome c when binding to the mitochondria in CD8 T cells and alveolar macrophages, and it has been reported that the protein increases severity in primary viral and secondary bacterial infections, and the protein is associated with high pathogenicity of an influenza virus.

Accordingly, in exemplary embodiment of the present invention, to examine the influence of the PB1-F2 protein on high pathogenicity of the 1918 strain of IAV, the PB1-F2 proteins of the 1918 strain and a low-pathogenic PR8 strain are compared to each other, thereby first identifying the correlation between the high pathogenicity and PB1-F2, and its molecular mechanism.

In one exemplary embodiment of the present invention, it was confirmed that, compared to the low-pathogenic PR8 strain of IAV, the PB1-F2 protein of the highly pathogenic 1918 strain has considerably low stability, which is caused by rapid protein degradation using a ubiquitin-proteasome system (refer to Examples 2 and 3).

In another exemplary embodiment of the present invention, as a result of analyzing expression patterns of the PB1-F2 proteins using a variety of PB1-F2 protein mutants prepared by substituting amino acids to find the reason for induction of degradation only in the PB1-F2 protein derived from the highly pathogenic 1918 strain, it was confirmed that the amino acids 68 and 69 on the amino acid sequence of the PB1-F2 protein affect stability of the protein (refer to Example 4).

In another exemplary embodiment of the present invention, in order to examine the influence of the instability of the PB1-F2 protein on a host defense system in IAV 1918 infection, the influence of the PB1-F2 protein on induction of type I IFN playing a very important role in the defense against a virus in innate immunity was analyzed. As a result, it was confirmed that, unlike the PR8 strain, IFNβ expression is inhibited by PB1-F2 of the 1918 strain, and a promoter activity of the PB1-F2 of the 1918 strain is also inhibited (refer to Example 5). In addition, by confirming that such a phenomenon does not occur when proteasome-dependent degradation is inhibited, and that the amino acids 68 and 69 identified to determine instability of the 1918 PB1-F2 protein affect the inhibitory response of type I IFN induction, it was confirmed that there is a correlation between the instability due to the proteasome-dependent degradation of the 1918 PB1-F2 protein and the inhibitory response of the type I IFN induction (refer to Example 6).

In still another exemplary embodiment of the present invention, it was confirmed that, among mouse models infected with each of the PR8 and 1918 strains of influenza virus, high virulence is exhibited in the mouse model infected with the 1918 strain of influenza virus, and it was also confirmed by using protein mutants prepared by substituting the amino acids 68 and/or 69 of a PB1-F2 protein that the amino acids at 68 and 69 residues of the PB1-F2 protein contribute to the high pathogenicity of the 1918 strain of IAV (refer to Example 7).

In yet another exemplary embodiment of the present invention, it can be known that the PB1-F2 protein of the 1918 strain inhibited IFNβ induction in the IAV-infected model, and therefore, due to improper viral clearance, a viral titer was maintained at a high level (refer to Example 8).

According to the exemplary embodiment of the present invention, a protein in which the amino acids 68 and 69 of the PB1-F2 protein are substituted, and preferably, a PB1-F2 protein mutant prepared by substituting the amino acids 68 and 69 with threonine and proline, respectively, like the 1918 strain, may be used as a marker for detecting a highly pathogenic influenza virus and used to detect a highly pathogenic virus by measuring the mutant.

Therefore, the present invention provides a composition for detecting a highly pathogenic virus, which includes an agent for measuring a protein mutant prepared by substituting the amino acids 68 and 69 of a PB1-F2 protein consisting of an amino acid sequence of SEQ ID NO: 1, and a kit for detecting a highly pathogenic virus, which includes the composition.

In the present invention, the protein mutant may be prepared by substituting the amino acids 68 and 69 with threonine and proline, respectively, and may consist of an amino acid of SEQ ID NO: 2.

In the present invention, the virus is preferably an influenza virus, but the present invention is not limited thereto.

In the present invention, the agent for measuring the protein mutant may be an antibody specifically binding to the protein, but the present invention is not limited thereto.

The term "antibody" used herein includes an immunoglobulin molecule immunologically having a reactivity with a specific antigen, and encompasses both of monoclonal and polyclonal antibodies. In addition, the antibody includes forms produced by genetic engineering such as a chimeric antibody (e.g., a humanized murine antibody) and a heterogeneous binding antibody (e.g., a bispecific antibody).

The detection kit of the present invention is composed of a composition, solution, or a device including one or more different components which are suitable for an analysis method.

In addition, the present invention provides a method for detecting a highly pathogenic virus, which includes measuring a protein mutant prepared by substituting the amino acids 68 and 69 of a PB1-F2 protein consisting of an amino acid sequence of SEQ ID NO: 1.

In yet another exemplary embodiment of the present invention, it was confirmed that the inhibitory response of IFNβ induction by the PB1-F2 protein of the 1918 strain occurs by inhibiting the function of DDX3 through the binding between the PB1-F2 protein and the intracellular DDX3 protein (refer to Example 9), and even in the presence of the PB1-F2 protein of the 1918 strain, the inhibition of the IFBβ induction is restored by treatment of a recombinant DDX3 protein, resulting in the induction of viral clearance (refer to Example 10).

Therefore, like the 1918 strain, by inhibiting the binding between the PB1-F2 protein prepared by substituting the amino acids 68 and 69 with threonine and proline, respectively, and intracellular DDX3, proliferation of highly pathogenic IAV may be inhibited.

Accordingly, in another aspect of the present invention, the present invention provides an antiviral composition against IAV, which includes an inhibitor of binding between DDX3 and a PB1-F2 protein as an active ingredient, and the PB1-F2 protein may be prepared by substituting the amino acids 68 and 69 of an amino acid sequence of SEQ ID NO: 1.

In the present invention, the PB1-F2 protein is prepared by substituting the amino acids 68 and 69 with threonine and proline, respectively, and may consist of an amino acid sequence of SEQ ID NO: 2.

The term "antiviral" used herein refers to weakening or dissipating the action of a virus having invaded a body by inhibiting viral proliferation in the body, and more specifically, by inhibiting viral proliferation by suppressing nucleic acid synthesis of a virus, gene expression of a virus, or viral replication, and in the present invention, this term is used for IAV, and more preferably, the 1918 strain of IAV (A/Brevig Mission/1/1918(H1N1)).

The DDX3, serving as a DEAD box family RNA helicase having various functions in cells, is involved in various stages of gene expression, that is, transcription, maturation of nucleic and mitochondrial mRNA, initiation of translation, and rearrangement of ribosomes and spliceosomes, and also involved in replication of hepatitis C virus (HCV) RNA, and it has been reported that the expression of DDX3 is reduced when liver cancer occurs due to HBV infection, and DDX3 is known to serve as a tumor-inhibitory protein. In addition, DDX3 is known to be involved in IFNβ induction caused by TANK-binding kinase 1 (TBK1) and Iκ-B kinase-epsilon (IκBKε)-dependent IRF3 activation. The DDX3 protein may consist of an amino acid sequence of SEQ ID NO: 3.

In the present invention, the binding inhibitor may be any one selected from the group consisting of a nucleic acid, a compound, a microbial culture medium or extract, a natural substance extract, a peptide, a substrate analog, an aptamer, and an antibody, but the present invention is not limited thereto.

In still another aspect of the present invention, the present invention provides a method for screening an antiviral substance against IAV, which includes:

(a) in vitro treating cells with a candidate substance;

(b) measuring binding between DDX3 and a PB1-F2 protein in the cells; and (c) selecting a substance decreasing the binding between the DDX3 and the PB1-F2 protein as an antiviral substance against IAV, compared to a group which is not treated with a candidate substance, and the PB1-F2 protein may be prepared by substituting the amino acids 68 and 69 on an amino acid sequence of SEQ ID NO: 1.

In the present invention, the candidate substance may be selected from the group consisting of a nucleic acid, a compound, a microbial culture medium or extract, a natural substance extract, a peptide, a substrate analog, an aptamer, and an antibody, and the nucleic acid may be selected from the group consisting of siRNA, shRNA, microRNA, anti-sense RNA, an aptamer, LNA, PNA, and a morpholino, but the present invention is not limited thereto.

In step (b), the measurement of the binding between DDX3 and the PB1-F2 protein may be carried out using a method selected from the group consisting of western blotting, immunoprecipitation, immunohistochemistry and immunofluorescence, but the present invention is not limited thereto.

Hereinafter, exemplary embodiments will be provided to help in understanding of the present invention. However, the following examples are merely provided to more easily understand the present invention, and the scope of the present invention is not limited to the following examples.

EXAMPLES

Example 1. Preparation and Experimental Methods 1-1. Cell Culture

A549 and 293T cells were incubated in a Dulbecco's modified Eagle's medium (DMEM, Gibco BRL, Gaithersburg, Md.) containing 10% fetal bovine serum (FBS, Gibco-BRL, Gaithersburg, Md.) inactivated by thermal treatment and 1% penicillin/streptomycin (Gibco-BRL, Gaithersburg, Md.) at 37° C. with 5% $CO_2$. U937 cells were incubated in an RPMI medium (Gibco-BRL, Gaithersburg, Md.) containing 10% FBS and 1% penicillin/streptomycin under the same conditions as used for the above cells. Transfection was carried out using Lipofectamine 2000 (Invitrogen) according to the manufacturer's protocols.

1-2. Preparation of Plasmids

PR8 PB1-F2 and 1918 PB1-F2 expression plasmids were cloned using pcDNA3.1 (+) vectors (Invitrogen) at EcoR I and Xho I restriction sites by PCR. Chimeric mutants, that is, mutants of an N-terminal domain of PR8 strain-derived PB1-F2 and a C-terminal domain of a 1918 strain; and an N-terminal of 1918 strain-derived PB1-F2 and a C-terminal domain of a PR8 strain, were amplified by PCR and then cloned in pcDNA3.1(+) vectors. In addition, PR8-derived PB1-F2 mutants prepared by amino acid substitution (R59K, R60Q, R59K/R60Q, R59K/R60Q/N66S, R59K/R60Q/N66S/I68T, and R59K/R60Q/N66S/I68T/L69P) were amplified by PCR and then cloned in pcDNA3.1(+) vectors. Primer sequences used in the experiment are shown in Table 1 below. In addition, a DDX3 expression plasmid was cloned in a pcDNA3.1(+) vector with Hind III and Xho I restriction sites, and IRF3 and TLR3 expression vectors were provided from a different research team of Yonsei University.

TABLE 1

| Primer | | Sequence | SEQ ID NO: |
|---|---|---|---|
| PB1-F2 | Forward | 5'-acc gaa ttc atg gac tac aag gat gac gac-3' | 4 |
|  | Reverse | 5'-acc ctc gag cta ctc gtg ttt gct gaa-3 | 5 |
| R59K | Forward | 5'-gtg tat tgg aag cga tgg ctt tcc ttg-3' | 6 |
|  | Reverse | 5'-caa gga aag cca tcg ctt cca ata cac-3' | 7 |
| R59K/R60Q | Forward | 5'-gtg tat tgg agg caa tgg ctt tcc ttg-3' | 8 |
|  | Reverse | 5'-caa gga aag cca ttg cct cca ata cac-3 | 9 |
| R59K/R60Q/N66S | Forward | 5'-gtg tat tgg aag cga tgg ctt tcc ttg-3' | 10 |
|  | Reverse | 5'-caa gga aag cca tcg ctt cca ata cac-3' | 11 |
| R59K/R60Q/N66S/I68T | Forward | 5'-ctt tcc ttg agg aat ccc acc ccg-3' | 12 |
|  | Reverse | 5'-cgg ggt ggg aft cct caa gga aag-3' | 13 |

TABLE 1-continued

| Primer | | Sequence | SEQ ID NO: |
|---|---|---|---|
| R59K/R60Q/N66S/ I68T/L69P | Forward Reverse | 5'-ctt gag gag tcc cat ccc ggt atc ttt-3' 5'-caa aga tac cgg gat ggg act cct caa-3' | 14 15 |
| I68T | Forward Reverse | 5'-ttg agg aat ccc acc ctg gta ttt ttg-3' 5'-caa aaa tac cag ggt ggg att cct caa-3' | 16 17 |
| L69P | Forward Reverse | 5'-agg aat ccc atc ccg gta ttt ttg aaa-3' 5'-ttt caa aaa tac cgg gat ggg aft cct-3' | 18 19 |
| I68T/L69P | Forward Reverse | 5'-ttg agg aat ccc acc ccg gta ttt ttg aaa-3' 5'-ttt caa aaa tac cgg ggt ggg aft cct caa-3' | 20 21 |
| T68I | Forward Reverse | 5'-ctt gag gag tcc cat ccc ggt atc ttt g-3' 5'-caa aga tac cgg gat ggg act cct caa-3' | 22 23 |
| P69L | Forward Reverse | 5'-gga gtc cca ccc tggta tct ttg aaa ac-3' 5'-gtt ttc aaa gat acc agg gtg gga ctc c-3' | 24 25 |
| T68I/P69L | Forward Reverse | 5'-ttg agg agt ccc atc ctg gta tct ttg aaa-3' 5'-ttt caa aga tac cag gat ggg act cct caa-3' | 26 27 |

1-3. Antibodies and Reagents

An anti-FLAG M2 monoclonal antibody, anti-HA, and an anti-β-actin antibody were purchased from Sigma (St. Louis, Mo.), and a Lamin A/C antibody was purchased from Cell Signaling Technology (Beverly, Mass.). Mouse polyclonal antibodies for detecting viral PB1-F2 proteins were prepared using a full sequence of recombinant PB1-F2 protein expressed in *E. coli*. A DDX3 antibody, and anti-mouse and anti-rabbit IgG horseradish peroxidase (HRP) antibodies were purchased from Santa Cruz Biotechnology (Santa Cruz, Calif.), and an anti-NP antibody was obtained from rabbits immunized with an NP protein (LabFrontier). MG132 and Poly(I:C) used in this example were purchased from Calbiochem (Germany) and InvivoGen, respectively.

1-4. Influenza Viruses

Influenza A/Puerto Rico/8/34(H1N1) virus (IAV (PR8)), PB1-F2 protein-depleted virus (IAV PB1-F2(−)), or a virus in which the amino acid sequence was substituted with a PB1-F2 protein of A/Brevig Mission/1/1918(H1N1) virus (IAV(1918)) in a PR8 virus backbone were used for in vitro and in vivo experiments. To prepare a PB1-F2 mutant virus using site-specific mutation, the 68Ile(ATC) and 69Leu (CTG) residues in a PB1-F2 protein of the A/Puerto Rico/8/34(H1N1) were substituted with Thr(ACC) and Pro (CCG), respectively. To obtain a recombinant virus expressing a mutated PB1-F2 protein, reverse genetics technology was used. Simply, seven cDNAs encoding a wild-type gene part and one mutated PB1 part were cloned in pHW2000 vectors and then transfected together into 293T cells. After 3 days, a supernatant was recovered to perform a plaque assay. The purified plaque was inoculated into MDCK cells to amplify viruses.

1-5. Influenza Virus Infection 6- to 8-week old female Balb/c mice were anesthetized and then infected with influenza viruses intranasally at 50 μL. The animal experiment was carried out by obtaining the approval of the Animal Experiment Ethics Committee of Konkuk University. For influenza virus infection into cells, A549 and U937 cells were washed with PBS and infected with influenza viruses at MOI 1. After 24 hours, the cells were recovered to perform RT-PCR and western blotting.

1-6. Real-Time PCR

Cells and mouse tissue were lysed with TRIzol to extract total RNA. Using 2 μg of the extracted RNA and M-MLV reverse transcriptase (iNtRON, Seoul, Korea), a reaction solution was prepared to have a final volume of 20 μL, thereby synthesizing cDNA, and then PCR was carried out using the cDNA as a template. The PCR was carried out under conditions of primary denaturation at 94° C. for 5 minutes, and 25 to 30 cycles of 94° C. (30 sec), 55 to 60° C. (30 sec) and 72° C. (30 sec), and final elongation at 72° C. for 5 minutes. Primer sequences used in the experiment are shown in Table 2 below. Quantitative real-time PCR was carried out using a SYBR Green PCR Master Mix (Applied Biosystems), and PCR amplification was performed using a real-time PCR apparatus manufactured by Applied Biosystems (ABI7500). Quantitative analysis of relative mRNA expression levels was performed using a ΔΔCt method, and the result is represented as a relative n-fold difference with respect to a calibrator ($RQ=2^{-\Delta\Delta ct}$).

TABLE 2

| Primer | | Sequence | SEQ ID NO: |
|---|---|---|---|
| IFNβ | Forward Reverse | 5'-gcc tgg cif cca tca tga ac-3' 5'-gag gca tca act gac agg tc-3 | 28 29 |
| PB1-F2 | Forward Reverse | 5'-atg gga ccg gaa cag gat aca cca-3' 5'-cta ctc gtg ttt gct gaa caa cct-3' | 30 31 |
| IL-1β | Forward Reverse | 5'-tca ggc agg ccg cgt cag tt-3' 5'-ttg ctg tga gtc ccg gag cgt-3 | 32 33 |

TABLE 2-continued

| Primer | | Sequence | SEQ ID NO: |
|---|---|---|---|
| IL-6 | Forward | 5'-agc gcc ttc ggt cca gtt gc-3' | 34 |
| | Reverse | 5'-tgc cag tgc ctc ttt gct gct-3' | 35 |
| IL-32 | Forward | 5'-gaa ggc ccg aat ggt aat gc-3' | 36 |
| | Reverse | 5'-tcg gca ccg taa tcc atc tc-3' | 37 |
| GAPDH | Forward | 5'-cgt ctt cac cac cat gga ga-3' | 38 |
| | Reverse | 5'-cgg cca tca cgc cac agt ft-3' | 39 |

1-7. Western Blotting

Cells were treated with a lysis buffer (25 mmol/L Tris-HCl, pH 7.5, 1% NP40, and protease cocktail) and centrifuged, thereby obtaining a supernatant from which intracellular proteins were eluted. 50 μg of proteins were loaded on a 12 to 15% acrylamide gel to perform SDS-PAGE, thereby separating the proteins by size, and then western blotting was performed. Protein detection using chemical fluorescence was carried out using ECL detection reagents (GE Healthcare, Buckinghamshire, UK), and expression levels of a target protein were determined using a Bio-Imaging Analyzer (LAS-4000, Fuji, Tokyo, Japan).

1-8. Luciferase Reporter Assay

Cells were transfected using Lipofectamine 2000, and after 48 hours, luciferase activity measured using a luciferase assay system (Promega, Madison, Wis., USA). β-galactosidase activity was measured for all samples, and the results were calibrated. The experiment was performed independently three times, and data were represented as mean±standard deviation (SD).

1-9. Measurement of IFNβ Content

A mouse lung tissue lysate was subjected to centrifugation at 10,000×g for 5 minutes, thereby obtaining a supernatant, and the supernatant was used to measure an IFNβ protein level using an IFNβ ELISA kit (R&D) according to the manufacturer's protocols.

1-10. Preparation of Protein Expression Plasmids

A pGE-LysRS-R9-DDX3 expression plasmid encoding LysRS-R9-DDX3 was manufactured using a pGE-LysRS-4 vector consisting of T7 promoter-LysRS-TEV protease recognition sequence-multicloning sites (KpnI-BamHI-EcoRV-SalI-HindIII) and a histidine tag. The LysRS-R9-DDX3 gene was amplified by PCR using a primer sequence of Table 3 below, and an amplification product was cleaved with KpnI/SalI and introduced into the KpnI/SalI site of pGE-LysRS-4.

TABLE 3

| Primer | | Sequence | SEQ ID NO: |
|---|---|---|---|
| LysRS-R9-DDX3 | Forward | 5'-gtc acg ggt acc cgt cgc cgt cgc cgt cgc cgt cgc cgt atg agt cat gtg gca gtg-3' | 40 |
| | Reverse | 5'-gtc acg gtc gac gtt acc cca cca gtc aac ccc ctg gga gtt a-3' | 41 |

Example 2. Analysis of PB1-F2 Protein Stability of IAV 1918 Strain

According to various studies, it has been known that the PB1-F2 protein of influenza virus has various functions, and recently, it has been reported that high morbidity of the 1918 pandemic influenza is associated with the PB1-F2 protein of a 1918 strain. Therefore, in this example, in order to examine molecular and functional characteristics of the 1918 influenza virus PB1-F2 protein, first, the PB1-F2 proteins of A/Brevig Mission/1/1918 (H1N1) (hereinafter, 1918 strain) and A/Puerto Rico/8/1934 (H1N1) (hereinafter, PR8 strain) influenza viruses were comparatively analyzed.

To this end, A549 and U937 cells were infected with the influenza viruses, that is, a PR8 strain (PR8), a virus of the PR8 strain in which the amino acid sequence was mutated with the PB1-F2 protein of a 1918 strain (PR8-PB1-F2 (1918)), and a PB1-F2 protein-depleted PR8 strain (PR8-PB1-F2(−)) at MOI 1 or 5 for 24 hours, and then subjected to western blotting to observe an expression pattern of the PB1-F2 proteins. As a result, as shown in FIG. 1, it was confirmed that the PR8 PB1-F2 protein is expressed, but the 1918 PB1-F2 protein was not detected. According to this result, it can be known that the PB1-F2 protein of the 1918 strain exhibits lower stability than that of the PR8 strain.

Example 3. Confirmation of Degradation of 1918 PB1-F2 Protein By Proteasome-Dependent Pathway Based on the result of Example 2, in order to see whether different PB1-F2 protein expression patterns between the PR8 strain and the 1918 strain are caused by degradation of a proteasome-mediated protein, the expression patterns of the PB1-F2 proteins were observed under a condition in which proteasome inhibitor MG132 was treated.

Figure 2A:
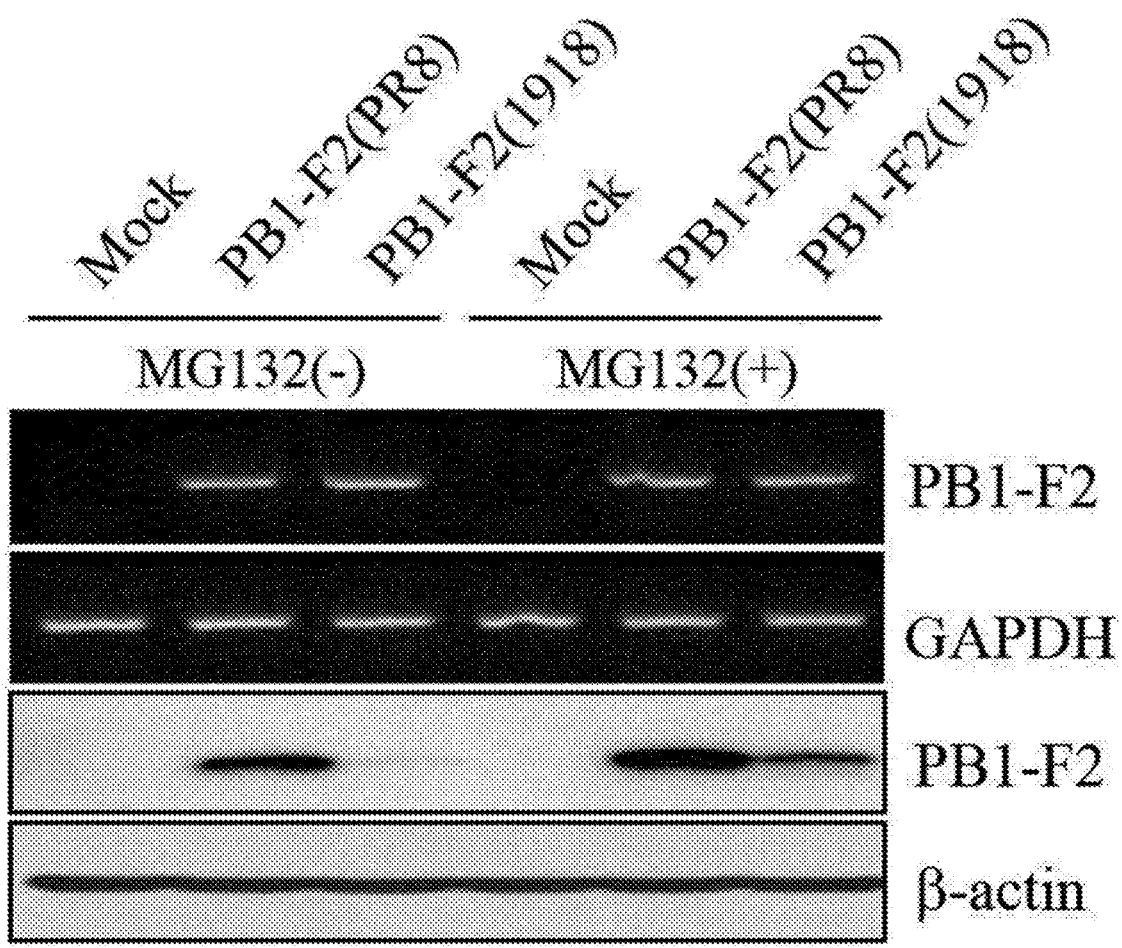

More specifically, A549 cells were transfected with each of Flag-tagged PB1-F2 expression plasmids of the PR8 strain and the 1918 strain, and treated with MG132 for 6 hours, and then the cells were collected. PB1-F2 mRNA and protein expression levels were analyzed through RT-PCR and western blotting. As a result, as shown in FIG. 2a, it was confirmed that, regardless of the treatment of MG132, 1918 PB1-F2 mRNA was detected, but the PB1-F2 protein was expressed only when MG132 was treated. According to this result, it can be known that the low stability of the 1918 PB1-F2 protein was associated with a proteasome-dependent pathway.

A ubiquitin-proteasome system is known to induce protein degradation and regulate functions of various proteins. To confirm whether the PB1-F2 protein is degraded by the ubiquitin-proteasome system, a ubiquitination assay was carried out. As a result, as shown in FIG. 2b, it can be known that the PB1-F2 protein is degraded by a ubiquitin-dependent proteasome pathway.

Example 4. Identification of Molecular Determinant of 1918 PB1-F2 Protein Stability Based on the results of Examples 2 and 3, in order to identify a molecular determinant determining stability of the PB1-F2 protein, a variety of PR8 and 1918 PB1-F2 mutant plasmids were manufactured and are shown in FIG. 3a.

Figure 3A:
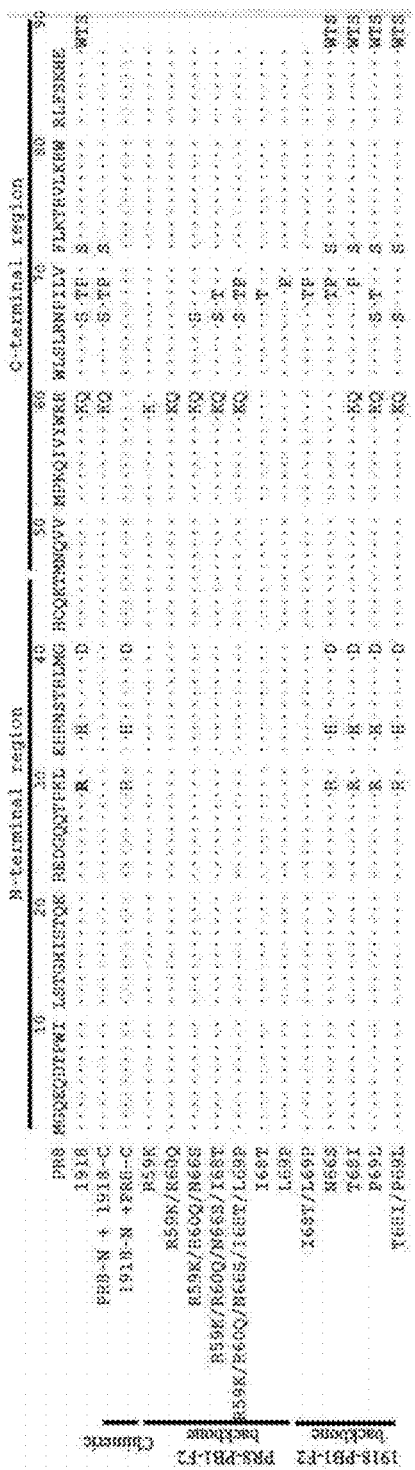
FIGS. 3a to 3d show the results of identifying a molecular determinant of the stability of a 1918 PB1-F2 protein, where
Figure 3B:
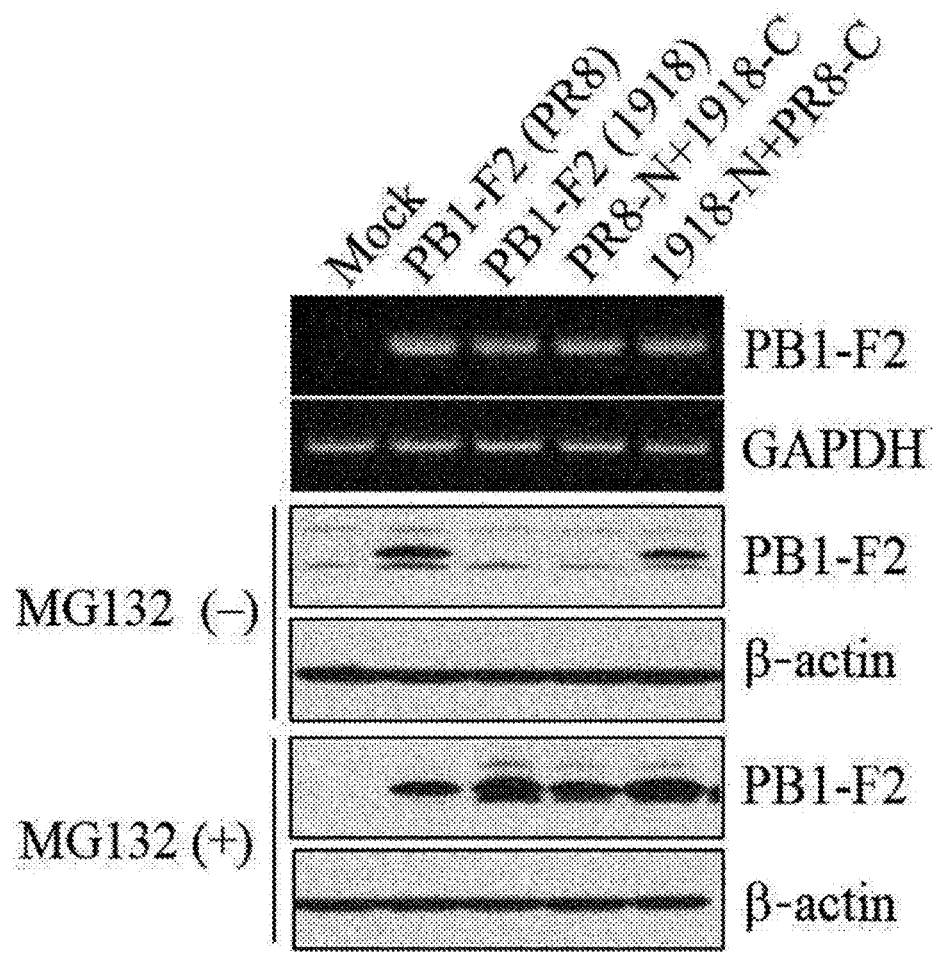

More specifically, A549 cells were transfected with each of PB1-F2 chimeric mutants PR8-N+1918-C and 1918-N+PR8-C as shown in FIG. 3a, and then PB1-F2 mRNA and protein expression levels were measured by RT-PCR and western blotting in the same manner as in Example 3. As a result, as shown in FIG. 3b, when the proteasome inhibitor MG132 was not treated, the PB1-F2 protein was not expressed in the PR8-N+1918-C-tranfected cells, and therefore it can be known that a part determining the stability of the protein is present at the C-terminal part of PB1-F2.

Figure 3C:
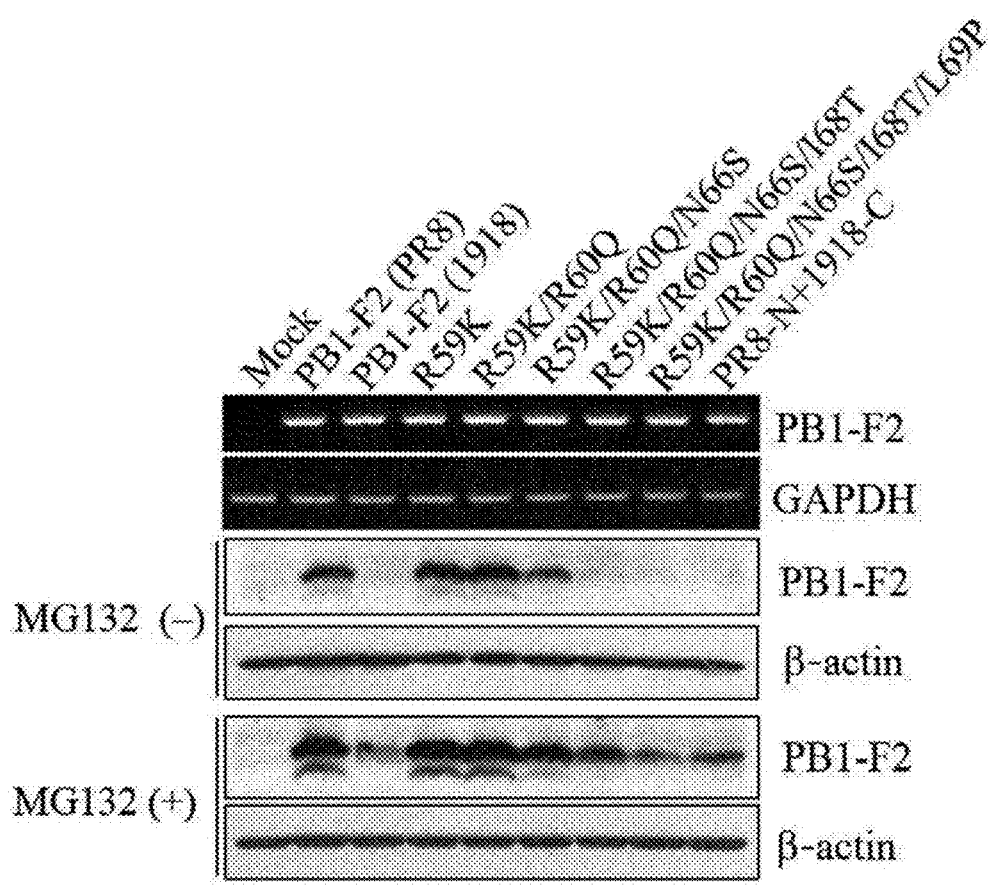

Afterward, in order to more specifically examine a stability determining part of the PB1-F2 protein, C-terminal point mutants were manufactured using a method of substituting some amino acids of the PR8 PB1-F2 sequence with those of 1918 PB1-F2, and then RT-PCR and western blotting were performed. As a result, as shown in FIG. 3c, it was confirmed that, when R59K/R60Q/N66S mutants were introduced while MG132 was not treated, the PB1-F2 protein was expressed, but when R59K/R60Q/N66S/I68T mutants and R59K/R60Q/N66S/I68T/L69P mutants were introduced, the PB1-F2 protein was not expressed. Therefore, it can be known that the amino acids 68 and 69 of the PB1-F2 protein are very important in the stability of the protein.

Figure 3D:
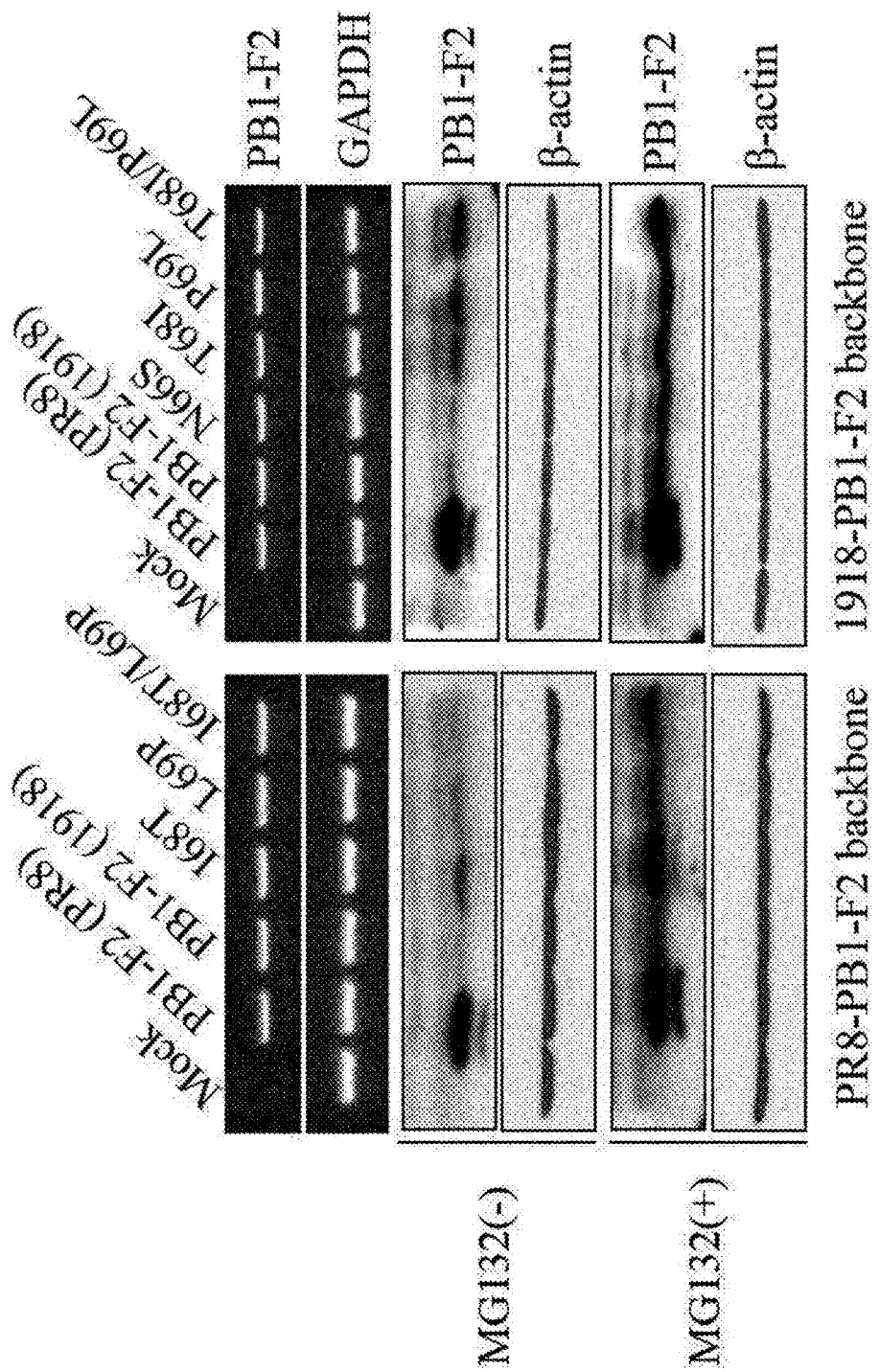

Further, to reconfirm that the amino acids 68 and 69 of the PB1-F2 protein are factors that determine instability of the protein, a plasmid was cloned after the amino acids 68 and 69 on the PR8 strain-derived PB1-F2 protein were substituted with those on the 1918 strain-derived PB1-F2 protein, and vice versa, and then each plasmid was transfected into cells, followed by RT-PCR and western blotting. As a result, as shown in FIG. 3d, when each or all of the amino acids 68 and 69 were substituted while MG132 was not treated, it was confirmed that expression of the PB1-F2 protein was inhibited in the backbone of the PR8 strain, and the protein expression was increased in the backbone of the 1918 strain. Accordingly, it can be known that the stability of the PB1-F2 protein was dependent on the amino acids 68 and 69.

Moreover, by the analysis of an intracellular position of each PB1-F2 clone, the PR8 PB1-F2 protein was primarily located in the mitochondria, but the 1918 PB1-F2 protein was dispersed in the cytoplasm or present in the nucleus. Therefore, it can be known that the amino acids 68 and 69 of the PB1-F2 protein are important for determining the intracellular position of the PB1-F2 protein. Such results indicate that Ile68 and Leu69 are molecular factors that determine the stability of the PB1-F2 protein.

Example 5. Confirmation of Inhibition of INFβ Secretion By 1918 PB1-F2 Protein

Figure 4A:
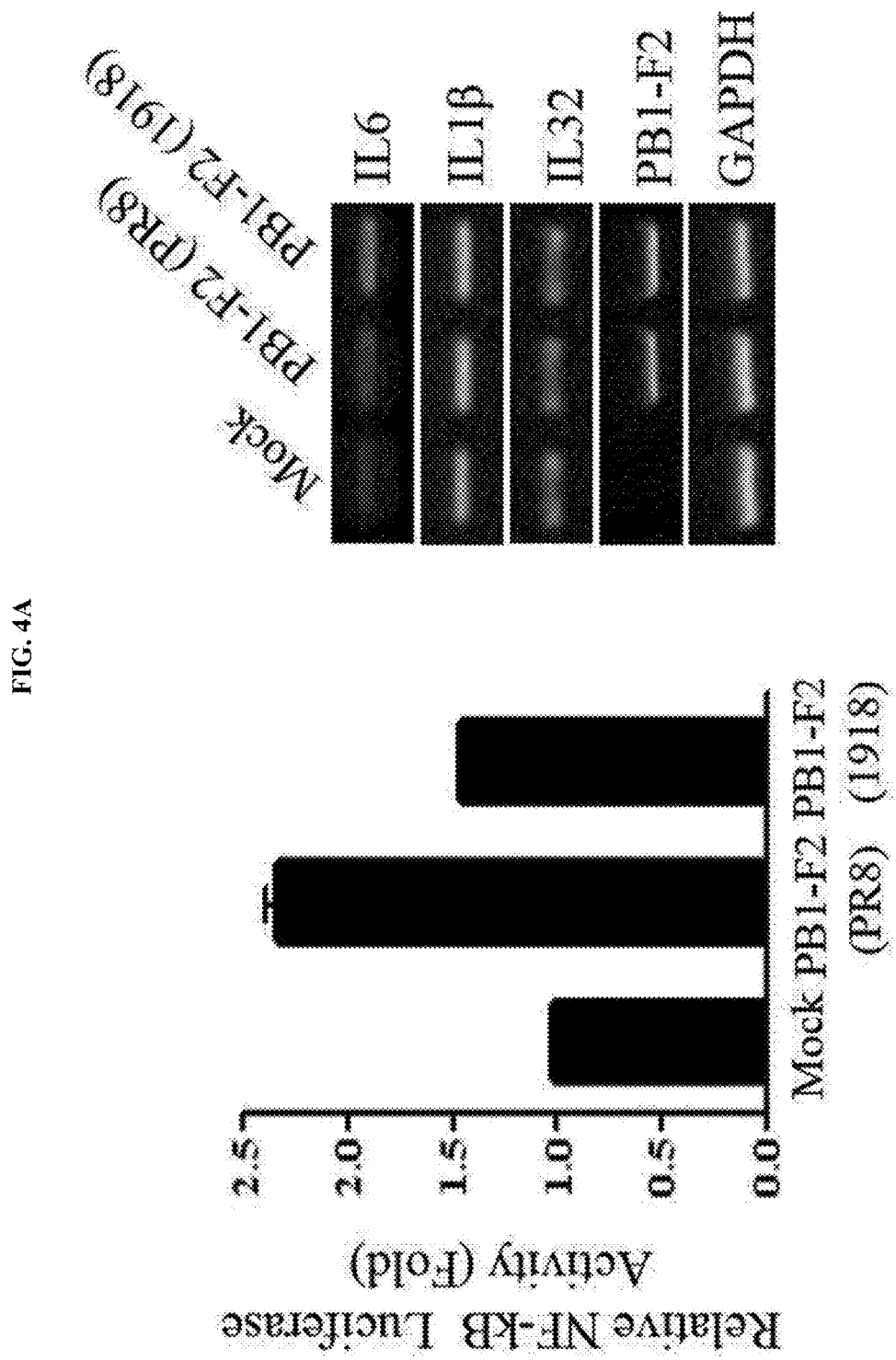
FIGS. 4a to 4d show that IFNβ induction is inhibited by a 1918 PB1-F2 protein, where

To examine the influence of instability of the 1918 PB1-F2 protein on a host, mRNA expression and NF-kB luciferase activity of a pro-inflammatory cytokine were analyzed. As a result, as shown in FIG. 4a, it was confirmed that there were no significant difference in the PB1-F2 proteins between the PR8 and 1918 strains.

A type I IFN response which is a main component of the innate immunity system is known to be very important in defense against viral pathogens. For example, according to various studies, it has been reported that the type I IFN plays a very important role in a host defense system against influenza infection. Therefore, to verify whether INFβ induction is influenced by the PB1-F2 protein, the inventors carried out semi-quantitative PCR and real-time PCR after A549 and U937 cells were transfected with plasmids expressing the PB1-F2 protein of each of the PR8 or 1918 strain.

Figure 4B:
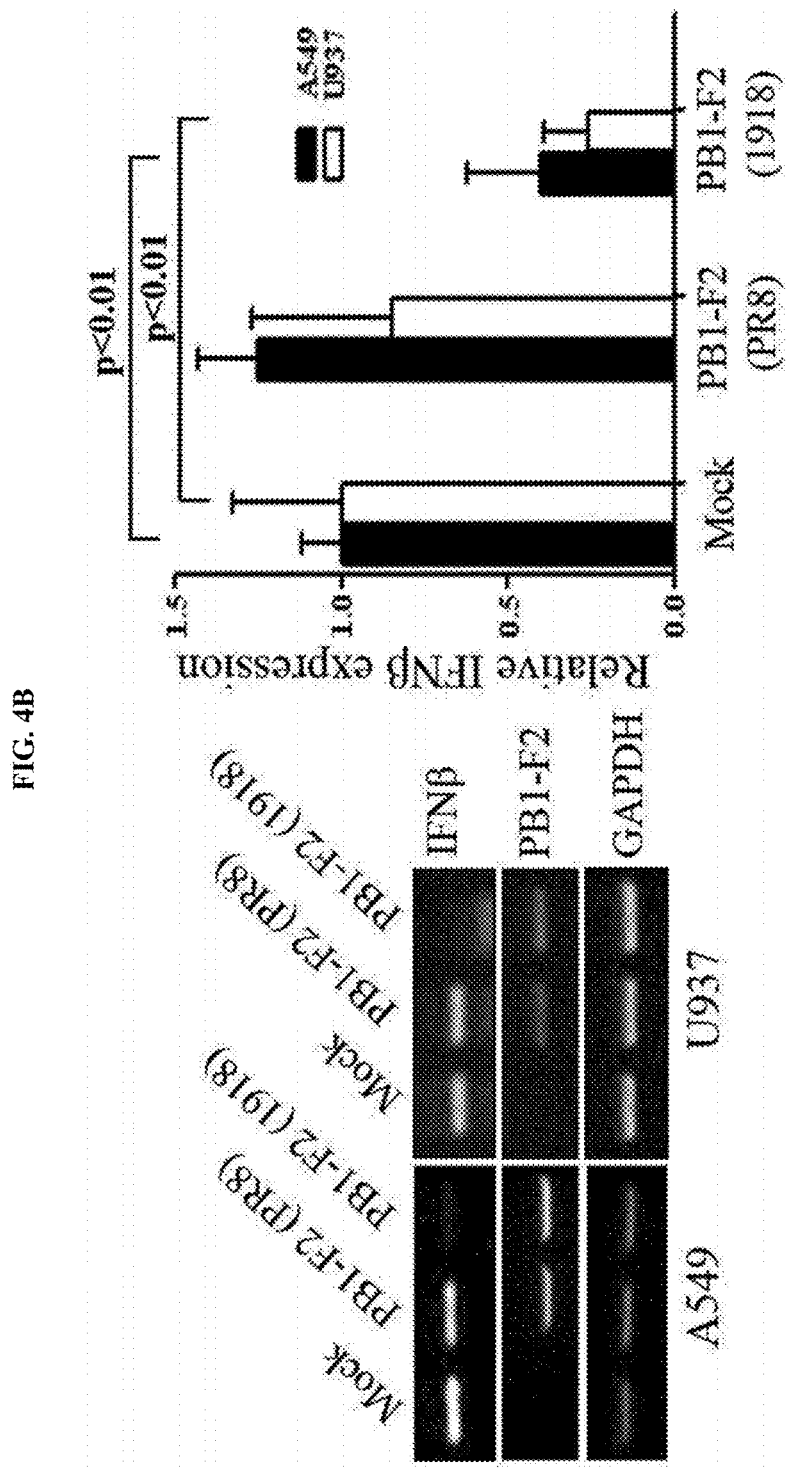
Figure 4C:
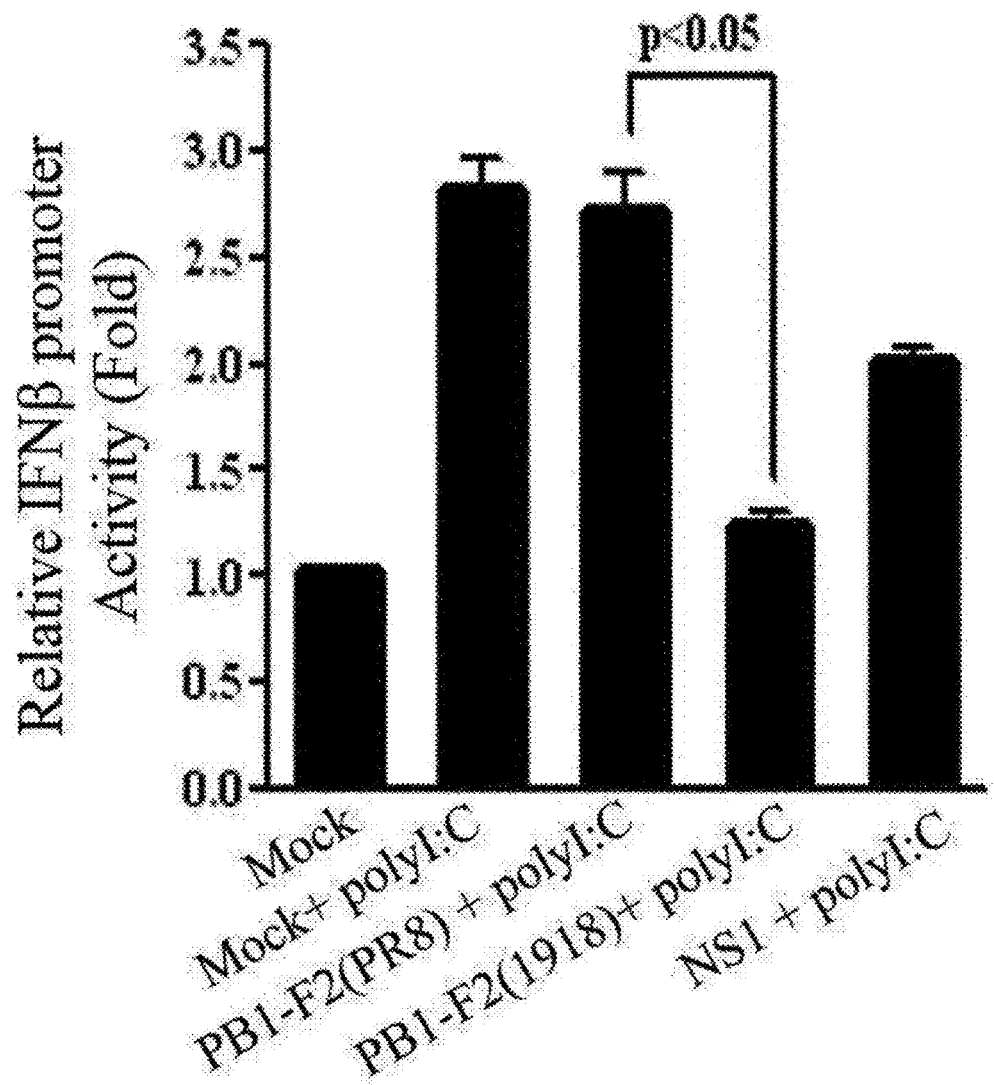

As a result, as shown in FIG. 4b, it was observed that 1918 PB1-F2 strongly inhibits intracellular IFNβ induction as opposed to the PR8 strain among the two types of cells. In addition, as shown in FIG. 4c, it was confirmed that U937 cells were transfected with an IFNβ luciferase reporter plasmid and a PB1-F2 or NS1 expression plasmid, treated with polyI:C before 12 hours of cell recovery, and subjected to luciferase analysis, resulting in inhibition of IFNβ promoter activity by 1918 PB1-F2.

Based on the above result, in order to investigate whether expression of the 1918 PB1-F2 protein in influenza virus-infected cells substantially affects expression of an IFNβ gene, A549 and U937 cells were inflected with IAV, that is, PR8 and 1918 strains at MOI 1, and then RT-PCR and western blotting were performed to observe a change in IFNβ mRNA and protein expression in cells.

Figure 4D:
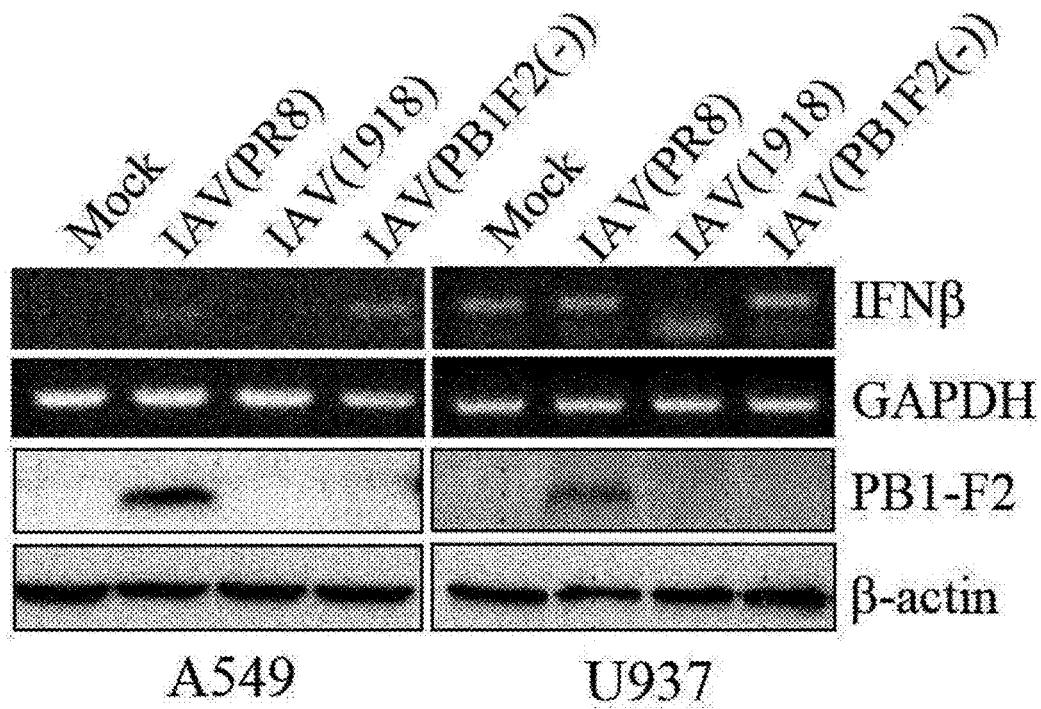

As a result, as shown in FIG. 4d, it was confirmed that the expression of IFNβ mRNA in cells induced by viral infection was inhibited by the 1918 PB1-F2 protein.

Such results indicate that the type I IFN response is inhibited by the 1918 PB1-F2 protein in virus-infected cells.

Example 6. Investigation of Correlation Between Proteasome-Dependent Degradation of 1918 PB1-F2 Protein and Inhibition of Type I IFN Induction From the results of Examples 2 and 3, it was confirmed that the 1918 PB1-F2 protein has significantly low stability, and based on this, it was intended to examine if there is a correlation between the stability of 1918 PB1-F2 and the inhibitory performance by the protein on IFNβ induction. To this end, A549 and U937 cells were transfected with PR8 and 1918 PB1-F2 expression plasmids, and after 18 hours, treated with a proteasome inhibitor such as MG132 for 6 hours, and then IFNβ expression was observed by semi-quantitative RT-PCR and western blotting.

Figure 5A:
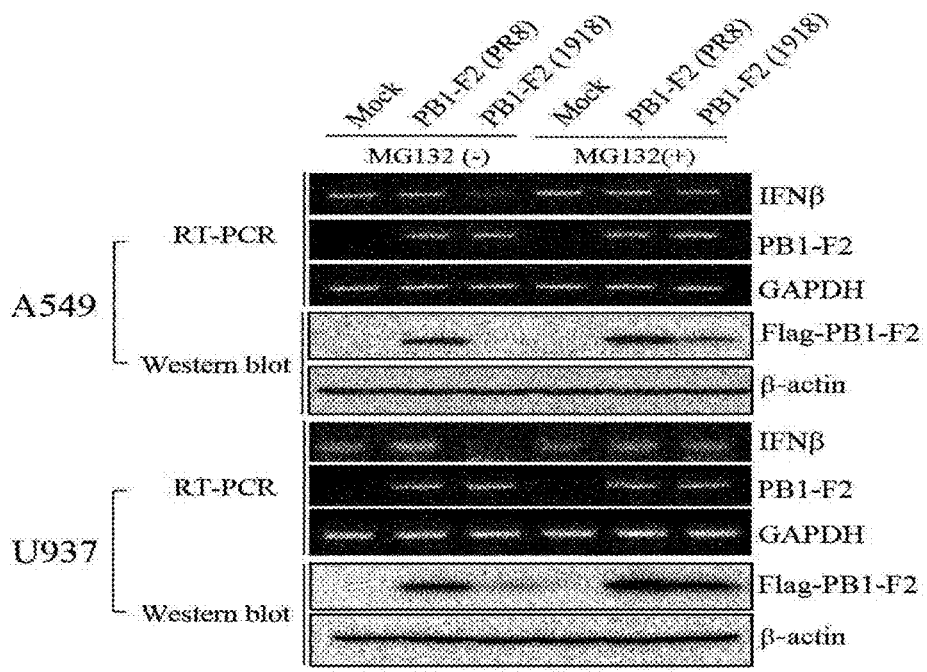
FIGS. 5a and 5b show the correlation between proteasome-dependent degradation of a 1918 PB1-F2 protein and inhibition of type I IFN induction, where

As a result, as shown in FIG. 5a, it was confirmed that the IFNβ mRNA and protein expression was inhibited by 1918 PB1-F2 when MG132 was not treated, but the IFNβ expression was not inhibited when MG132 was treated. Such a result indicates that the stability of PB1-F2 has an important effect on the inhibition of IFNβ induction by 1918 PB1-F2.

Further, to verify if the amino acids 68 and 69 of 1918 PB1-F2 identified as the molecular factors determining stability of the PB1-F2 protein affect inhibition of the IFNβ expression, after mutants in which the amino acids 68 and 69 of PB1-F2 were transfected into the A549 cells, IFNβ expression was observed by semi-quantitative RT-PCR and western blotting.

Figure 5B:
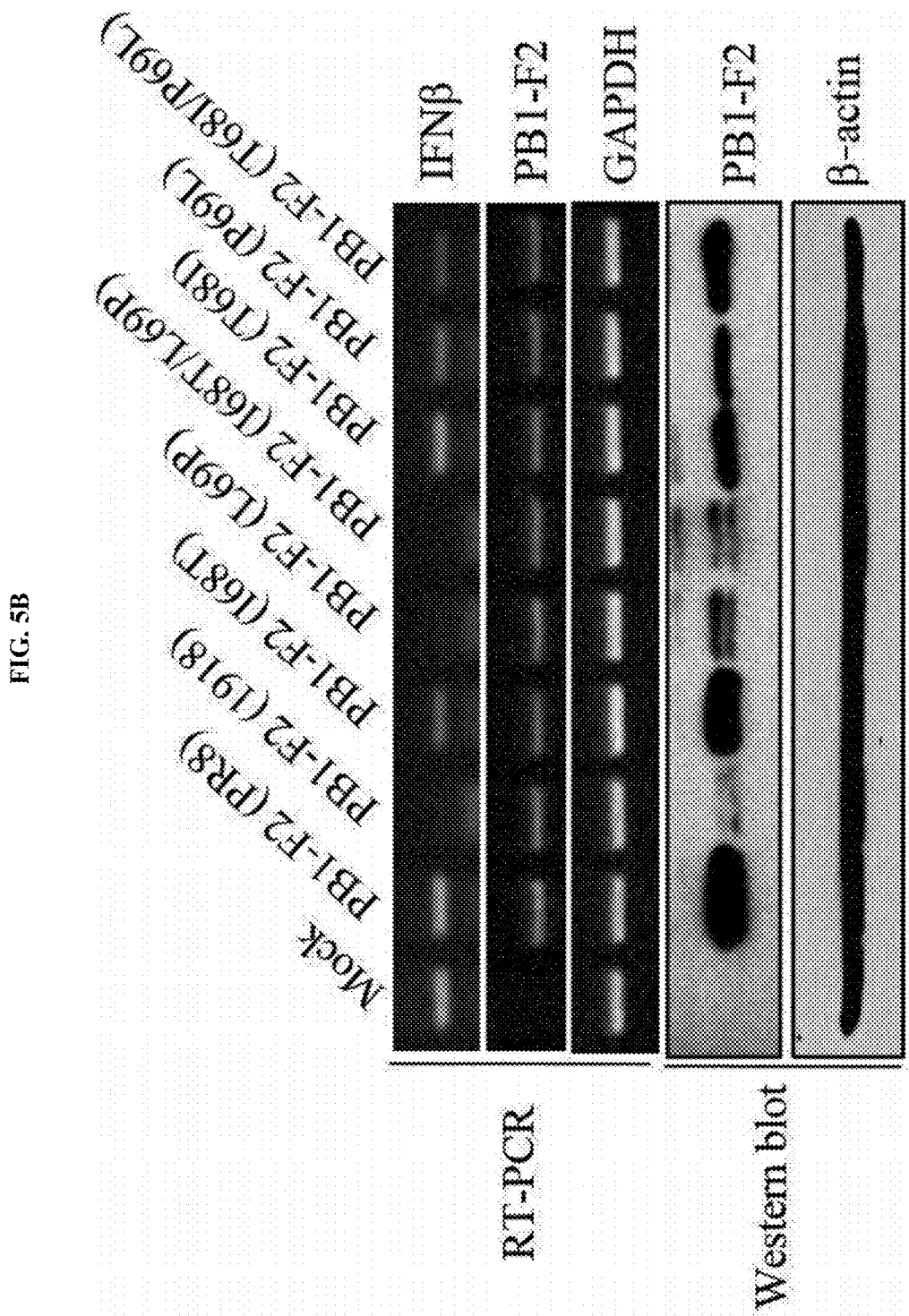

As a result, as shown in FIG. 5b, it was confirmed that when the amino acids 68 and 69 of PB1-F2 were substituted with tryptophan (T) and/or proline (P), mRNA and protein expression of IFNβ (I68T, L69P, and I68T/L69P) was inhibited.

Such results indicate that there is a correlation between the proteasome-dependent degradation of the 1918 PB1-F2 protein and the strong expression inhibitory performance of the type I IFN.

Example 7. Investigation of Influence of Amino Acids 68 and 69 of 1918 PB1-F2 on Pathogenicity of IAV 1918 Strain To examine the influence of the PB1-F2 protein on viral pathogenicity when a host is infected with the 1918 strain of IAV, a change in body weight and a survival rate of a mouse were observed for 14 days after influenza viruses of PR8 or 1918 strains were intranasally administered into the mouse at $5×10^2$ PFU or $1×10^3$ PFU.

Figure 6A:
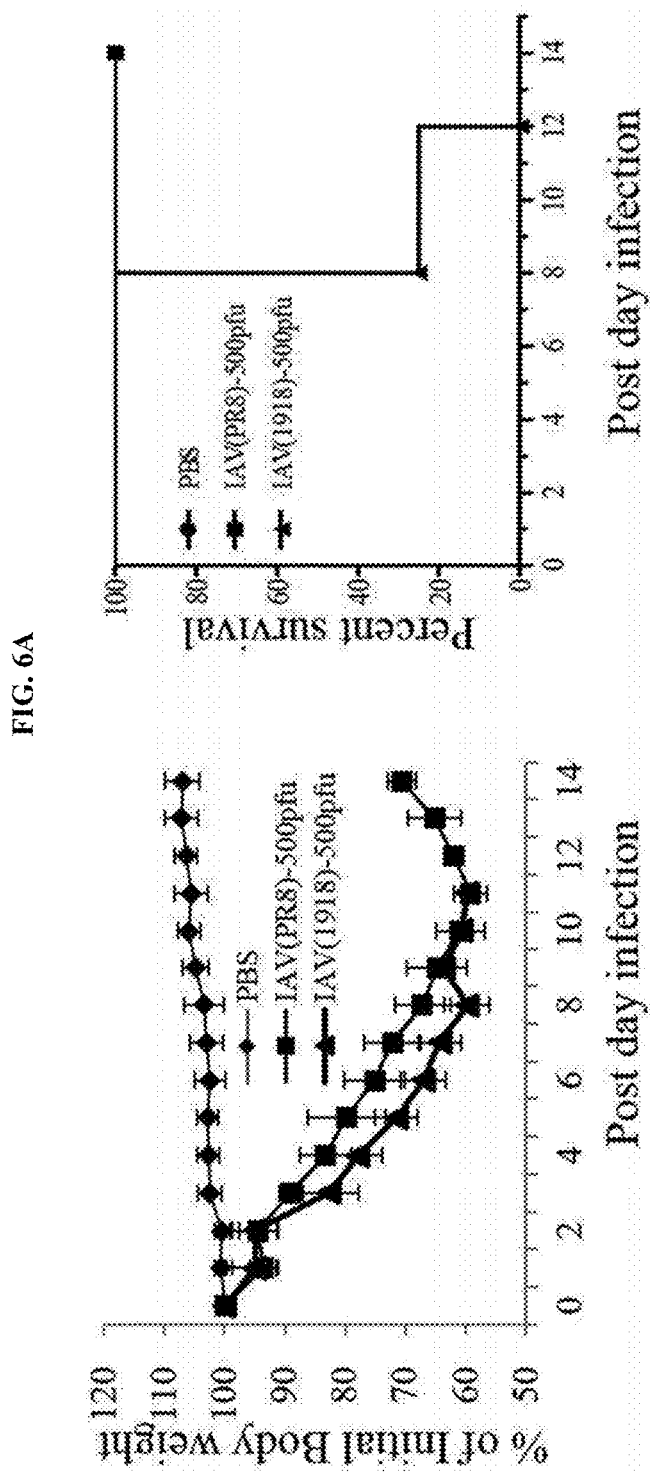
Figure 6B:
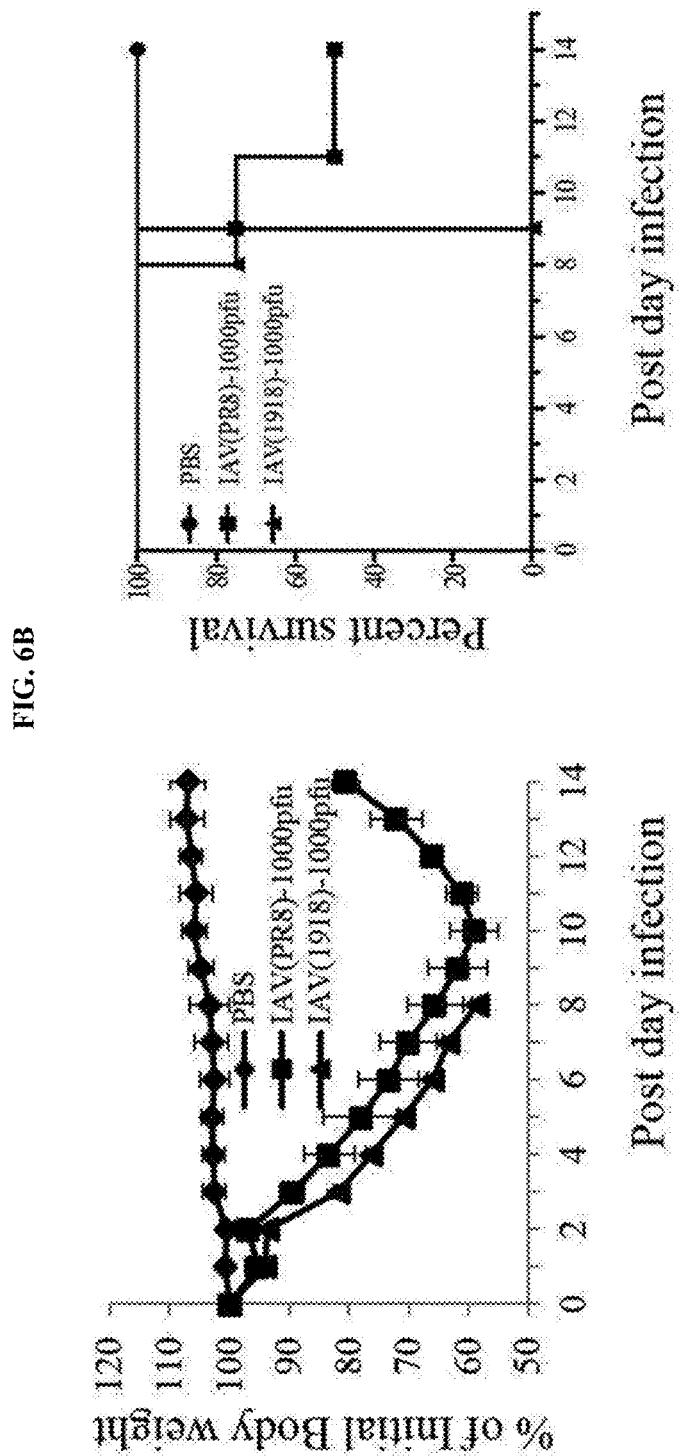

As a result, as shown in FIGS. 6a and 6b, it was confirmed that the mouse exhibits higher virulence when infected with the influenza viruses of the 1918 strain, compared to those of the PR8 strain.

Further, from the results of Examples 4 and 6, it was confirmed that the amino acids 68 and 69 of the PB1-F2 protein are factors that determine instability of the protein and IFNβ induction, and based on this, it was intended to verify if the amino acid position has an important effect on the pathogenicity of influenza viruses. To this end, it was observed that mice were infected with mutated influenza viruses prepared by substituting the amino acids 68 and 69 of the PR8 PB1-F2 protein with those of the 1918 PB1-F2, and then changes in body weight and survival rate were observed.

Figure 6C:
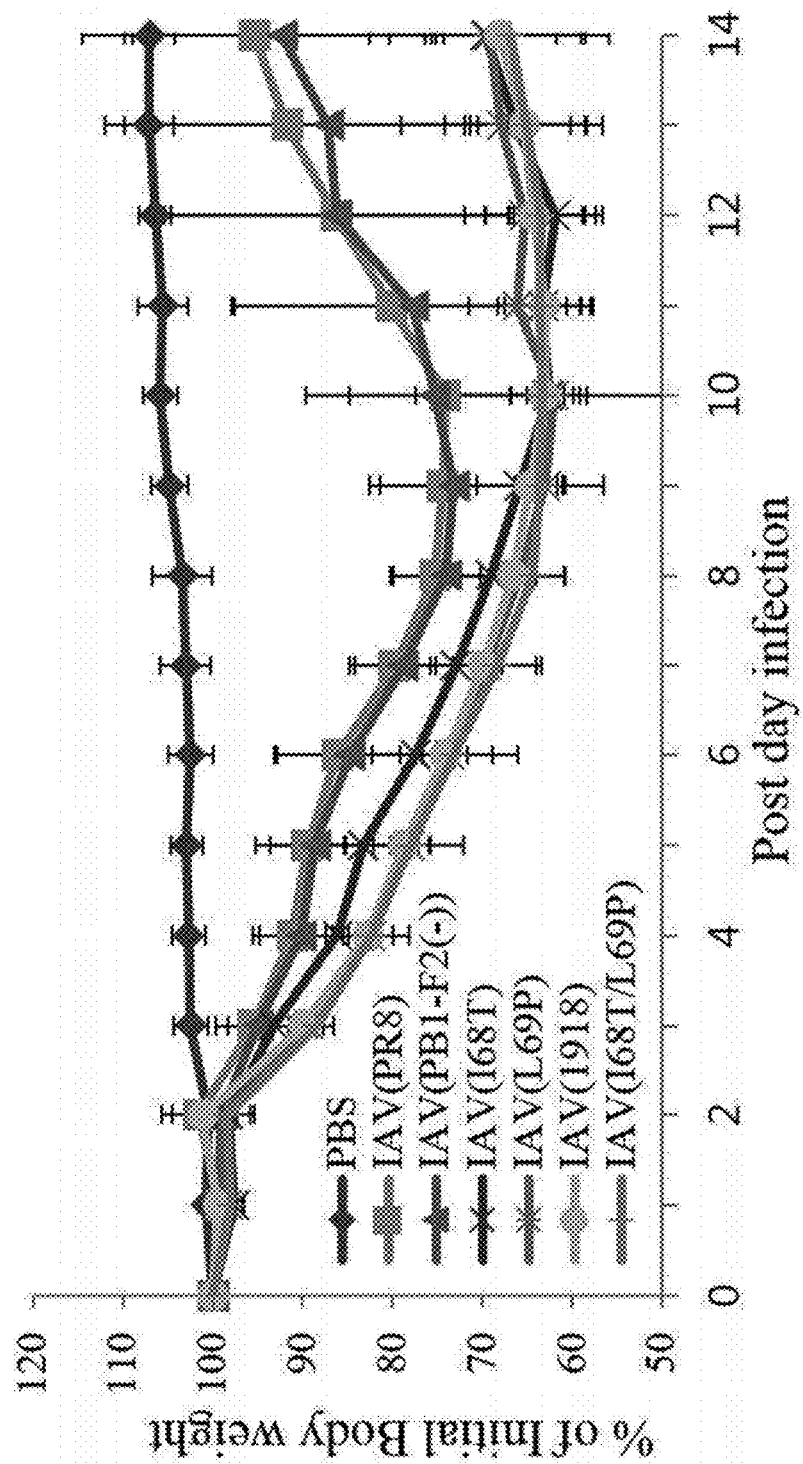

As a result, as shown in FIG. 6c, compared to the mice infected with the PR8 strain and the PB1-F2 protein-depleted virus (PB1-F2(−)), the body weight of the mice infected with the mutant viruses (I68T, L69P, and I68T/L69P) was decreased to a similar degree as that of the mice infected with the 1918 PB1-F2 viruses.

Figure 6D:
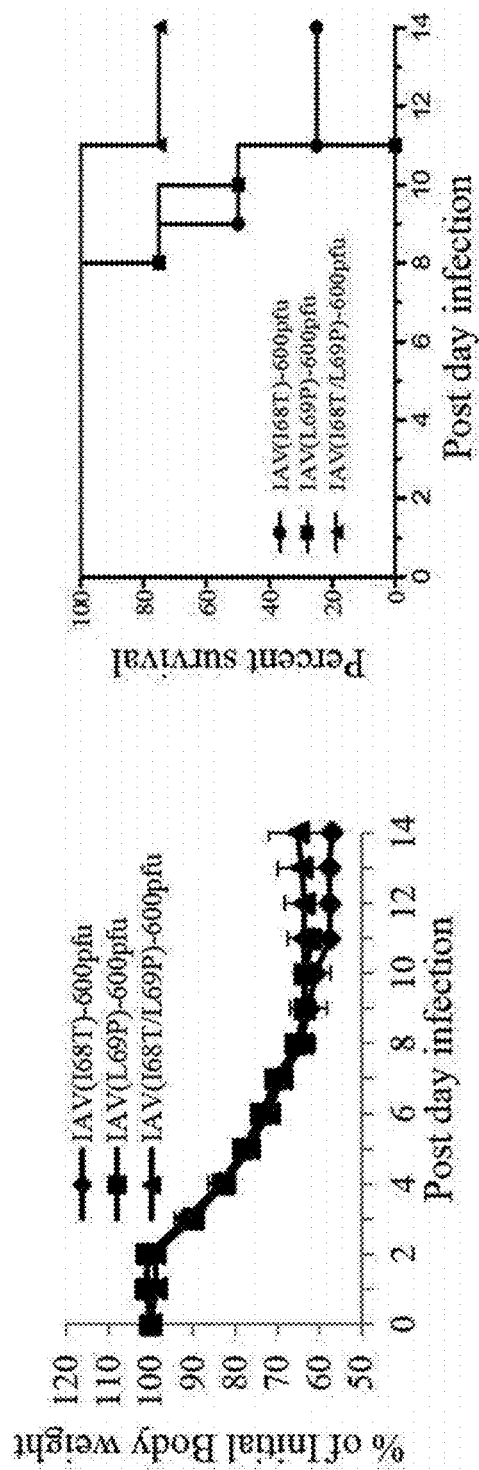
Figure 6E:
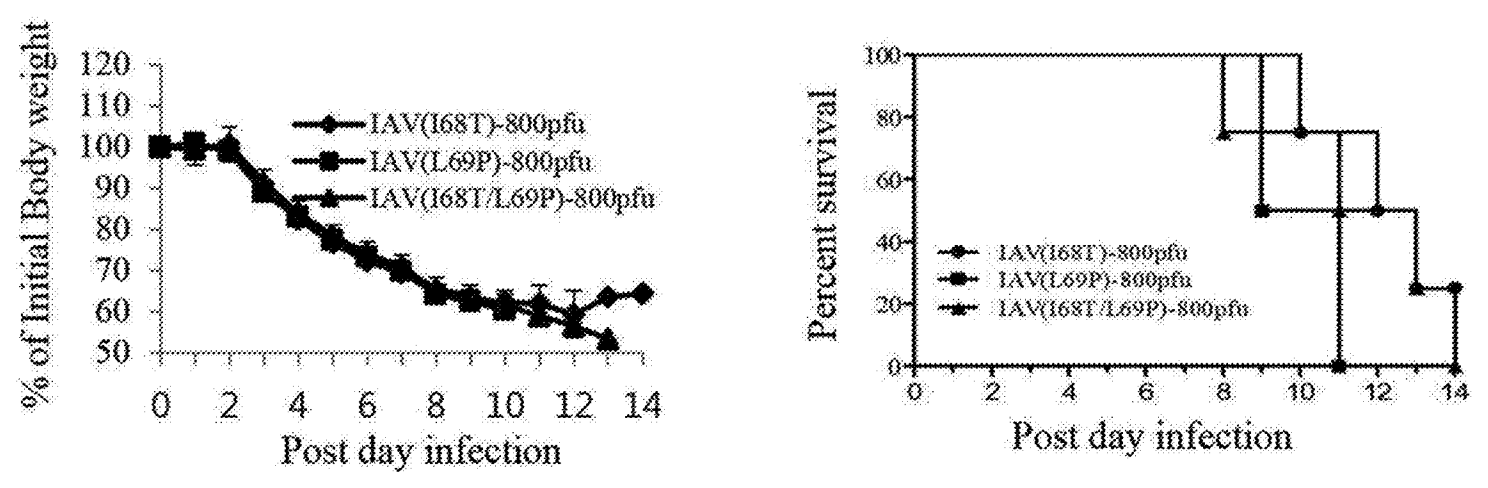
Figure 6F:
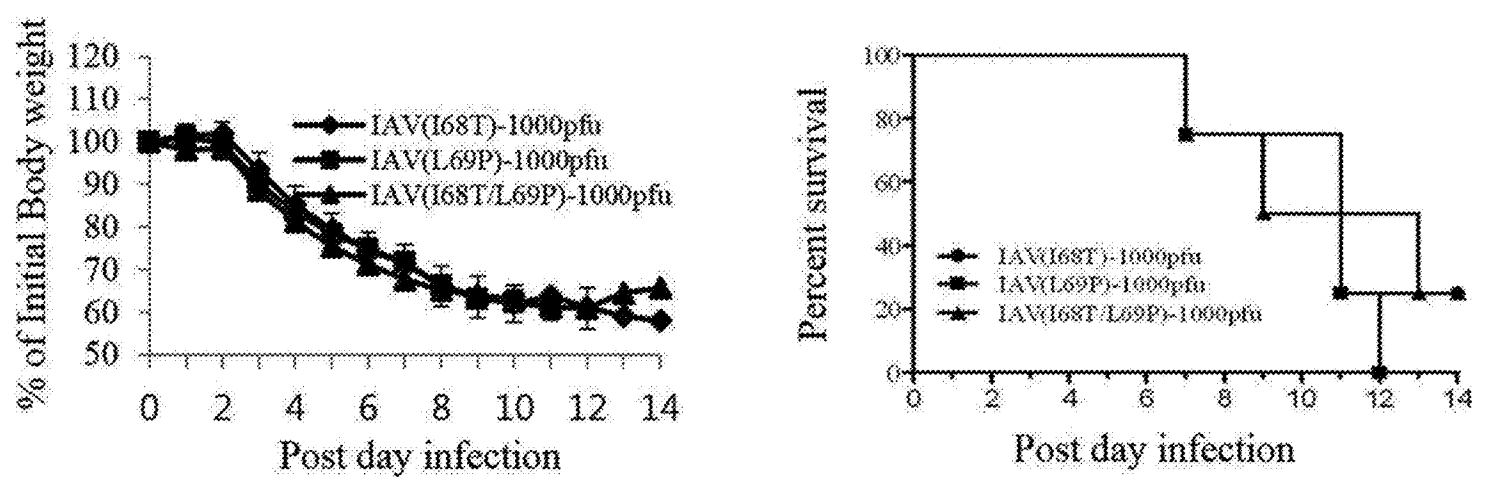

Furthermore, in order to investigate the influence of the amino acids located at the above positions on the virulence of 1918 PB1-F2, mice were infected with I68T, L69P, and I68T/L69P mutant viruses at various contents ($6×10^2, 8×10^2$, and $1×10^3$ PFU), and then body weights and survival rates were measured. As a result, as shown in FIGS. 6d to 6f, it was confirmed that all of the amino acids 68 and 69 of the 1918 PB1-F2 protein contribute to viral virulence.

From the above results, it can be known that the amino acids 68 and 69 of the PB1-F2 protein contribute to high pathogenicity of the 1918 strain of IAV.

Example 8. Confirmation of In Vivo Inhibition of IFNβ Induction By 1918 PB1-F2

Figure 7A:
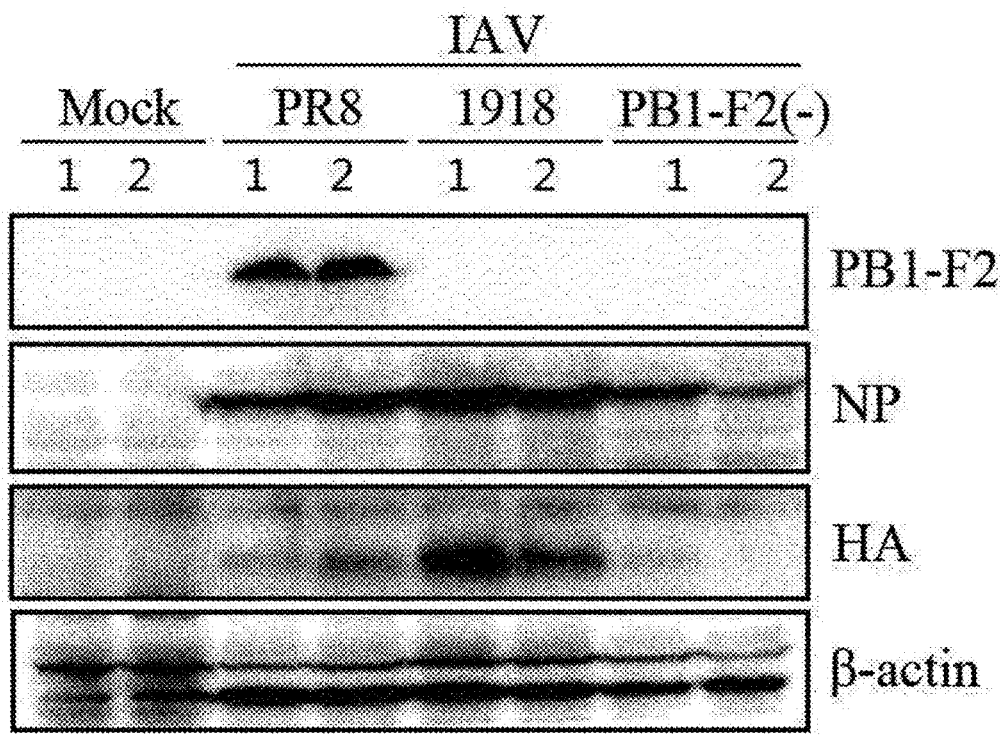

To verify if the 1918 PB1-F2 protein substantially inhibits the IFNβ induction in an influenza virus-infected model, mice were infected with each type of influenza viruses such as PR8, 1918, or PB1-F2-depleted 1918 (PB1-F2(−)) at $5×10^2$ PFU, and after two days, expression levels of viral proteins such as PB1-F2, NP, and HA in mouse lung tissue were analyzed by western blotting. As a result, as shown in FIG. 7a, it was confirmed that HA and NP viral proteins were more highly expressed in the mice infected with the 1918 strain of virus than in the mice infected with the PR8 strain of virus.

Figure 7B:
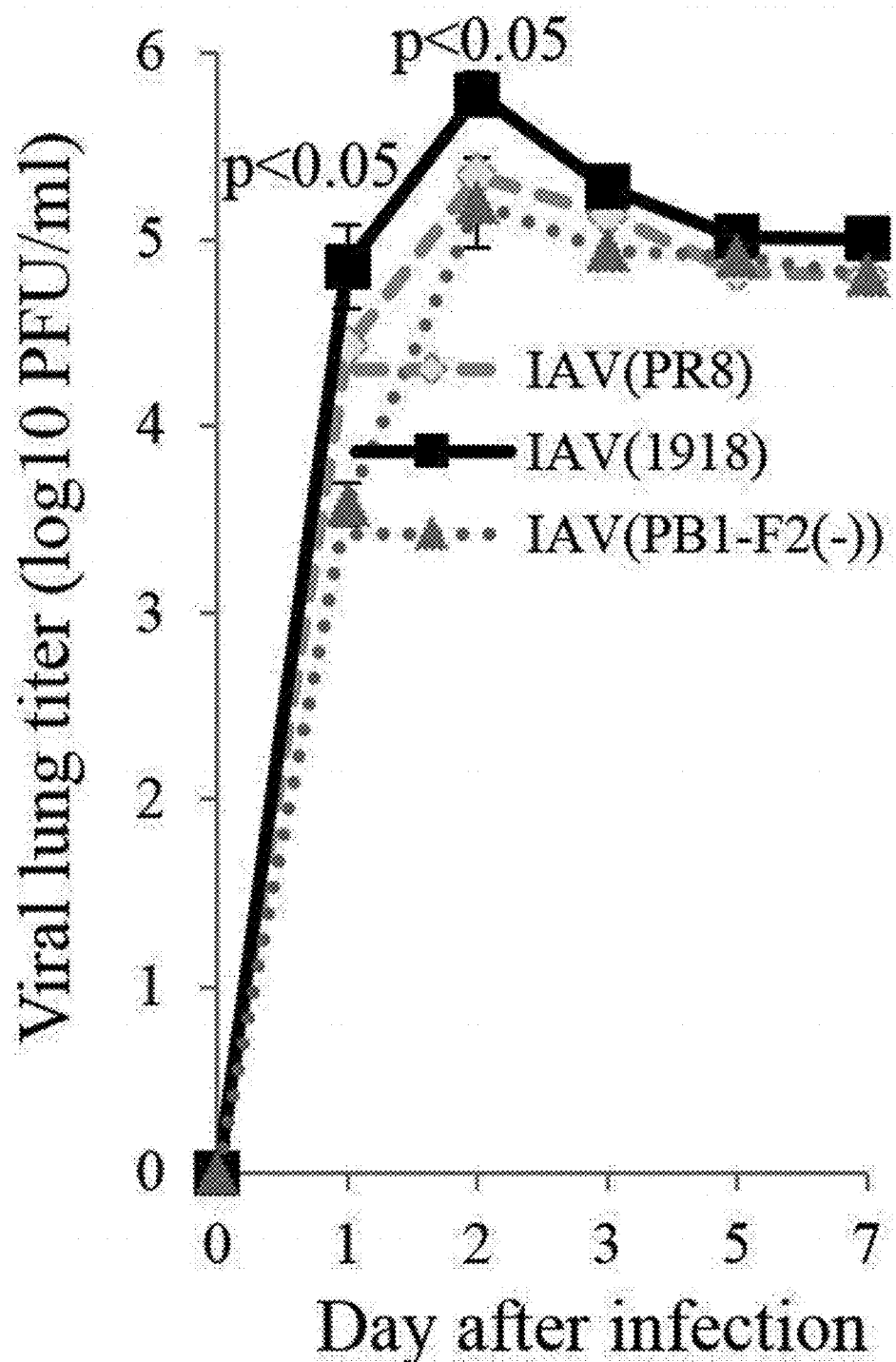

To examine whether the expression level of such a viral protein is associated with virus replication, a virus titer was measured on a lung tissue lysate through plaque assay. As a result, as shown in FIG. 7b, it was confirmed that a titer of the 1918 strain virus was approximately 10-fold higher than those of the PR8 strain virus and the PB1-F2-depleted virus, indicating that there is a defect on the process of viral clearance of the 1918 strain.

Therefore, based on the result, to verify if infection with the 1918 strain virus inhibits the IFNβ induction in the lung tissue of mice infected with each type of virus, the expression level of IFNβ mRNA was measured by performing RT-PCR. As a result, as shown in FIG. 7c, it was confirmed that only when infected with the 1918 strain of virus, the IFNβ expression is considerably inhibited.

Figure 7D:
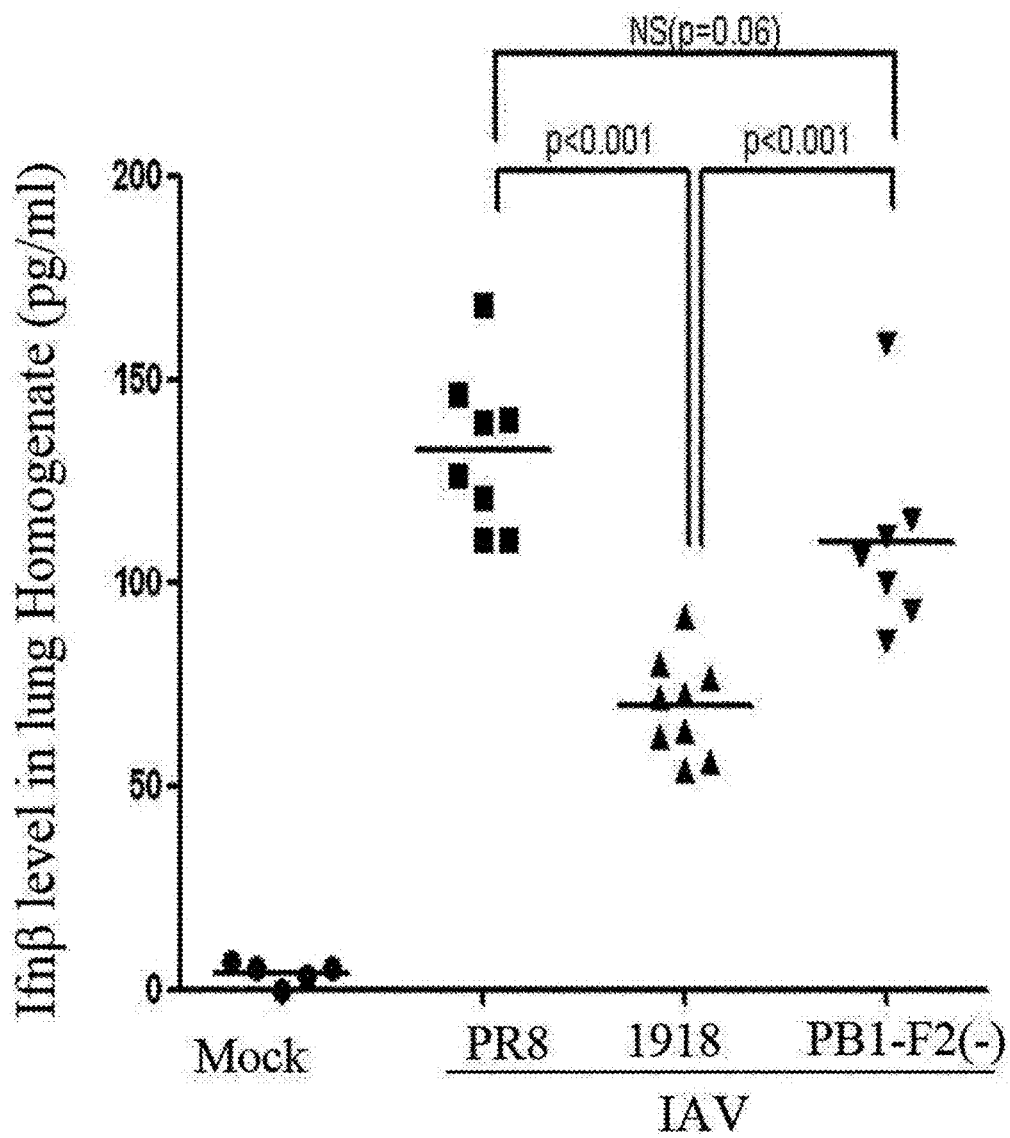

In addition, when an amount of the IFNβ protein secreted from the lung of a mouse infected with each type of virus was measured through ELISA, as shown in FIG. 7d, it was confirmed that the amount of the IFNβ protein secreted from the mouse infected with the 1918 strain of virus was lower than those of the mice infected with the PR8 strain of virus and the PB1-F2-depleted virus.

The results indicate that PB1-F2 inhibits the IFNβ induction in the mouse infected with the 1918 strain of virus.

Example 9. Identification of Inhibition of IFNβ Induction Through Binding Between 1918 PB1-F2 and DDX3

Figure 8A:
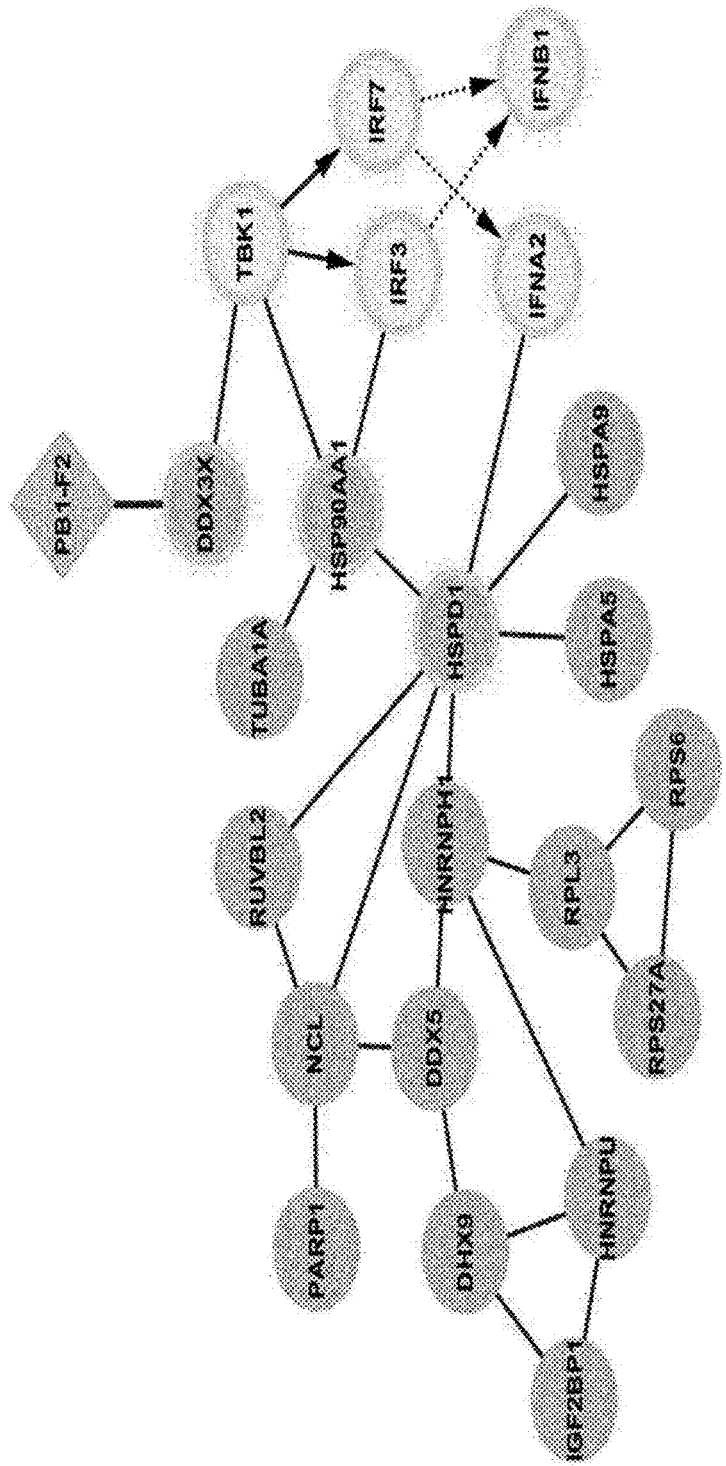

To identify a molecular mechanism for inhibiting IFNβ induction by 1918 PB1-F2, proteins interacting with 1918 PB1-F2 were analyzed by IP. As a result, it was seen through LC-MS/MS analyses that a total of 134 types of proteins interacted with 1918 PB1-F2. Further, biological functions of the proteins interacting with PB1-F2 were analyzed using the ingenuity pathway analysis (IPA) program, and the analysis focused on viral infection-related proteins. As a result, as shown in FIG. 8a, DDX3X, HSP90AA1, and HSPD1 proteins were deduced, and it is known that these proteins are associated with viral infection and thus interact with TBK1, IRF3 and INFA2 proteins.

Figure 8B:
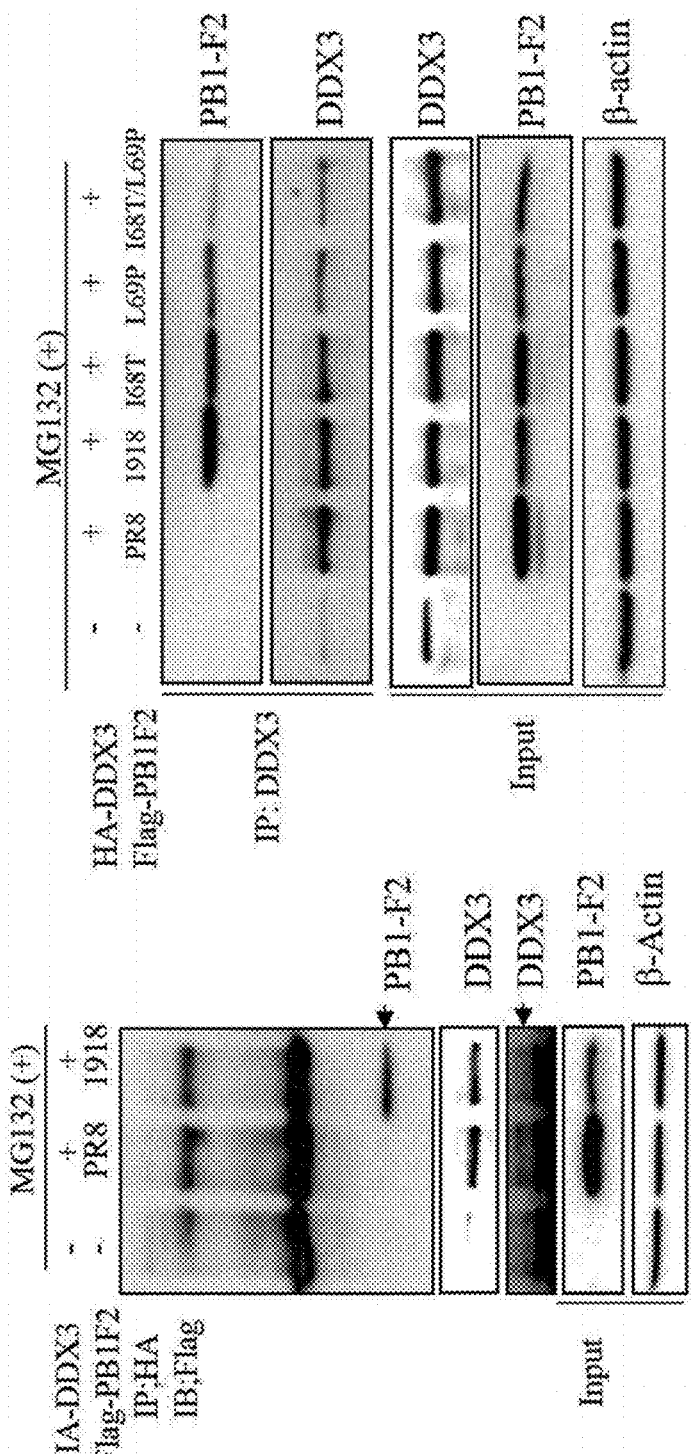

Therefore, in order to assess the interaction between 1918 PB1-F2 and DDX3 by focusing on DDX3 deduced from the above result, A549 cells were transfected with a plasmid expressing DDX3 (HA-tagged DDX3) and a PR8 or 1918 PB1-F2 expression plasmid (Flag-tagged PB1-F2), and then subjected to IP under the condition of MG132 treatment. As a result, as shown in FIG. 8b, it was confirmed that 1918 PB1-F2 binds to DDX3. Further, it was also confirmed that mutant proteins (I68T, L69P, and I68T/L69P) prepared by substituting the amino acids 68 and 69 of PR8 PB1-F2 with those of 1918 PB1-F2 interacted with DDX3 by transfecting expression plasmids of the mutant proteins and performing the same experiment as described above.

Figure 8C:
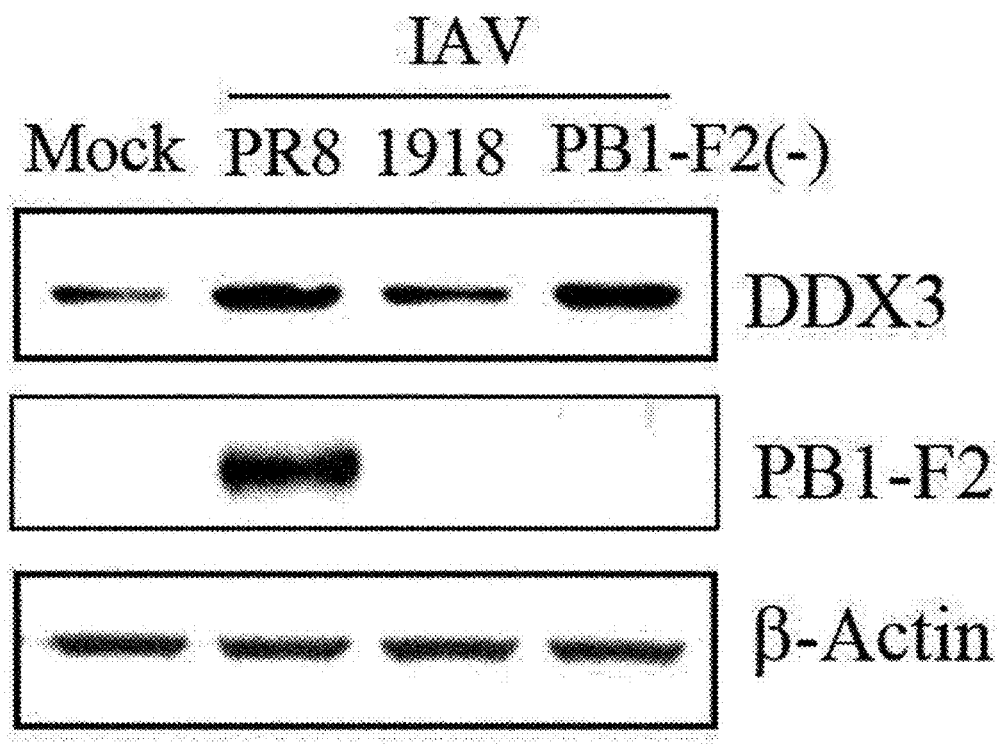
Figure 8D:
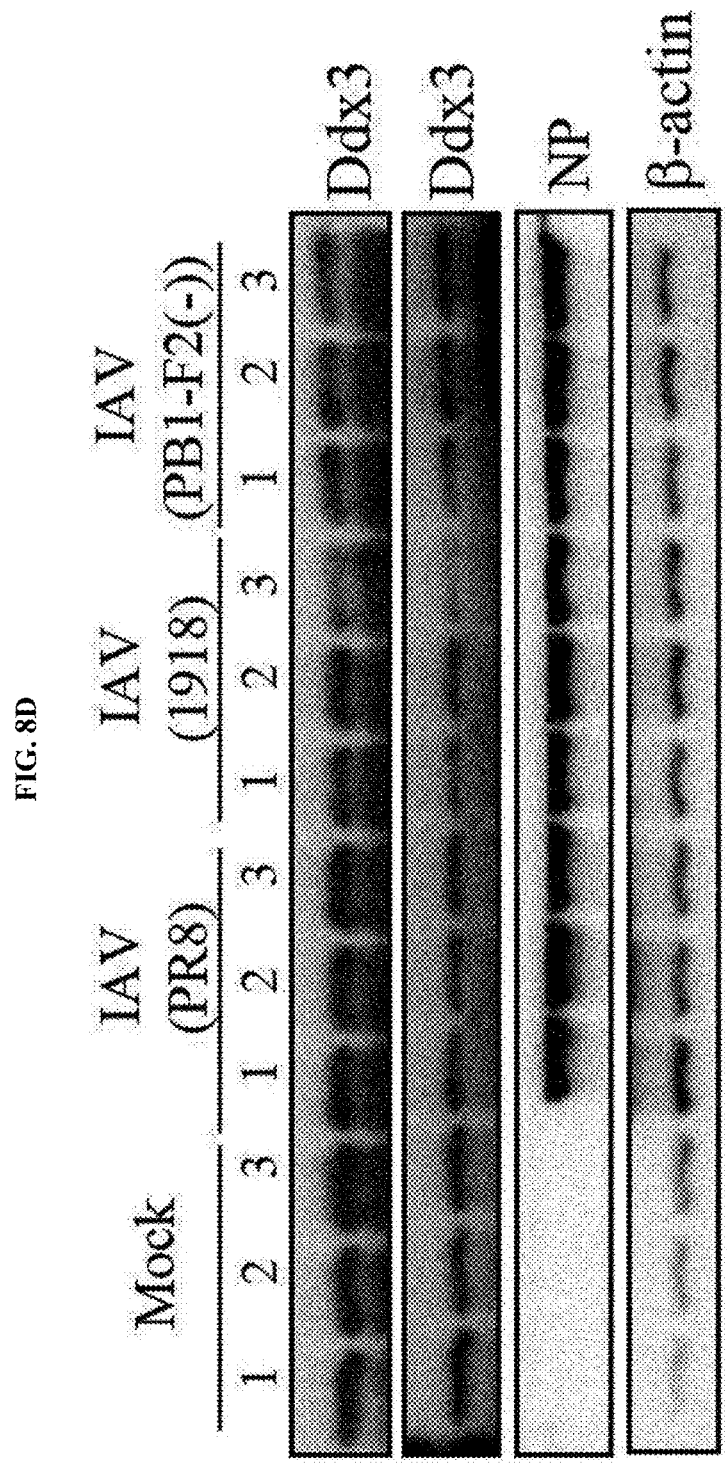

Subsequently, to verify whether DDX3 was inhibited by the 1918 PB1-F2 protein, A549 cells were infected with each influenza virus. As a result, as shown in FIG. 8c, DDX3 expression was decreased by the 1918 PB1-F2 protein. In addition, it was confirmed that intracellular DDX3 expression was decreased as shown in FIG. 8d even in the lung tissue of a mouse infected with each type of influenza virus.

Further, since IRF3 phosphorylation and nuclear translocation occur in the IFNβ induction, the inventors assessed nuclear translocation of IRF3 to investigate whether the nuclear translocation of IRF3 was inhibited by 1918 PB1-F2. As a result, as shown in FIG. 8e, while the nuclear translocation of IRF3 was decreased by the 1918 PB1-F2 protein, such a phenomenon was restored by DDX3 addition. Such results indicate that IFNβ induction is inhibited by the interaction of 1918 PB1-F2 with DDX3.

Figure 8F:
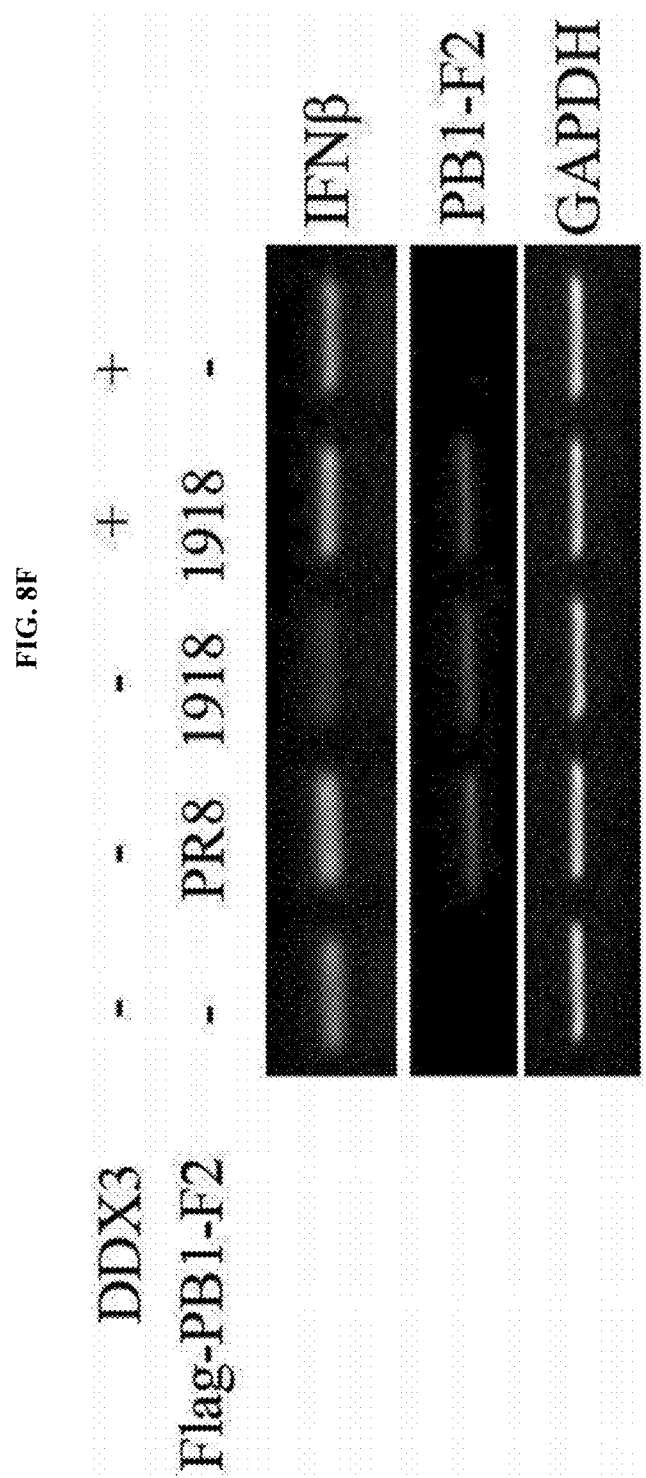

To verify the result again, A549 cells were transfected with the PR8 and 1918 PB1-F2 expression plasmids and the DDX3 expression plasmid, and then a change in expression level of IFNβ mRNA was analyzed by trans-complementation assay, and as a result, as shown in FIG. 8f, it was confirmed that IFNβ mRNA expression is decreased by 1918 PB1-F2, but Fnβ mRNA expression is increased again by DDX3 expression.

The results indicate that IFNβ induction was inhibited by binding the 1918 PB1-F2 protein to DDX3.

Example 10. In Vivo Confirmation of Decrease in Pathogenicity of 1918 PB1-F2 Influenza Virus By Treatment of Recombinant DDX3

To prove a mechanism of inhibiting IFNβ secretion by the interaction between 1918 PB1-F2 and DDX3 identified by the results of the above examples, the role of DDX3 in IFNβ induction was verified. To this end, an in vivo experiment was carried out to verify whether the inhibition of the IFNβ induction can be repaired by the administration of the recombinant DDX3 protein into a mouse model infected with the 1918 influenza virus, and an experimental process is illustrated in FIG. 9a.

Figure 9B:
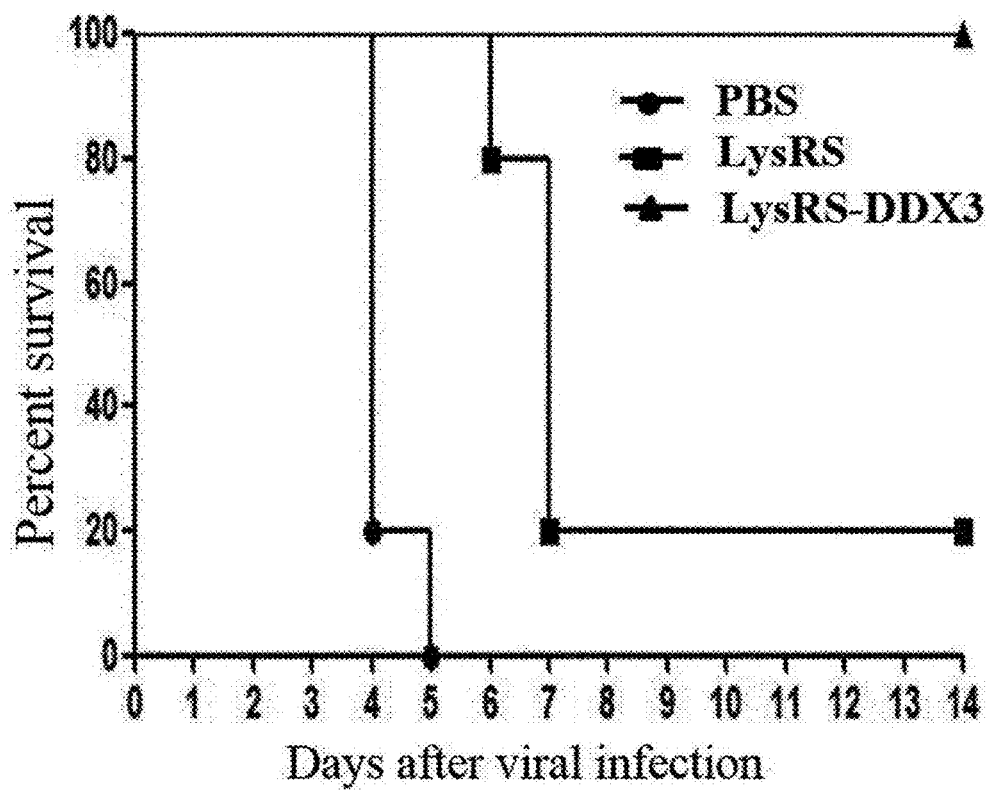
Figure 9C:
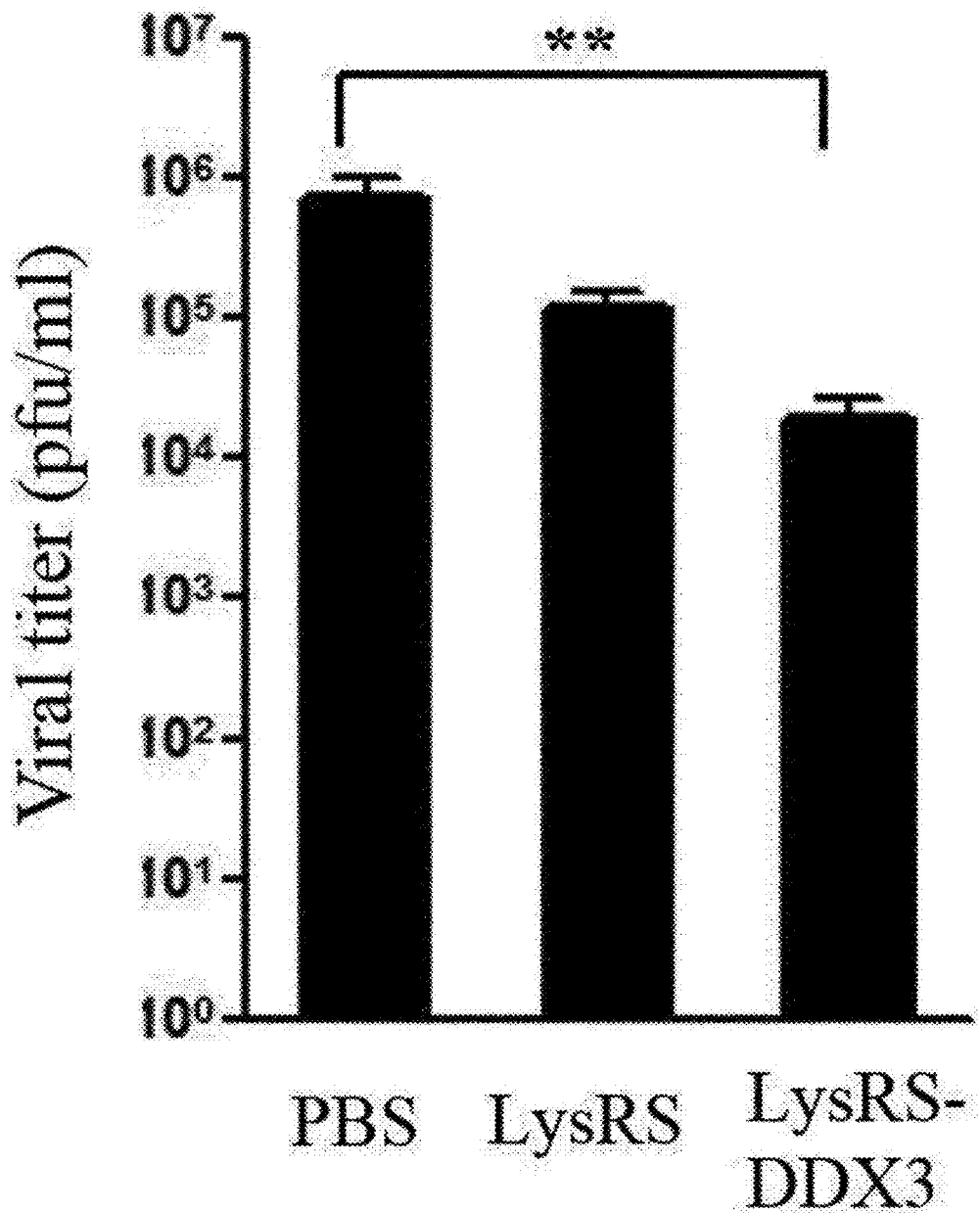
Figure 9D:
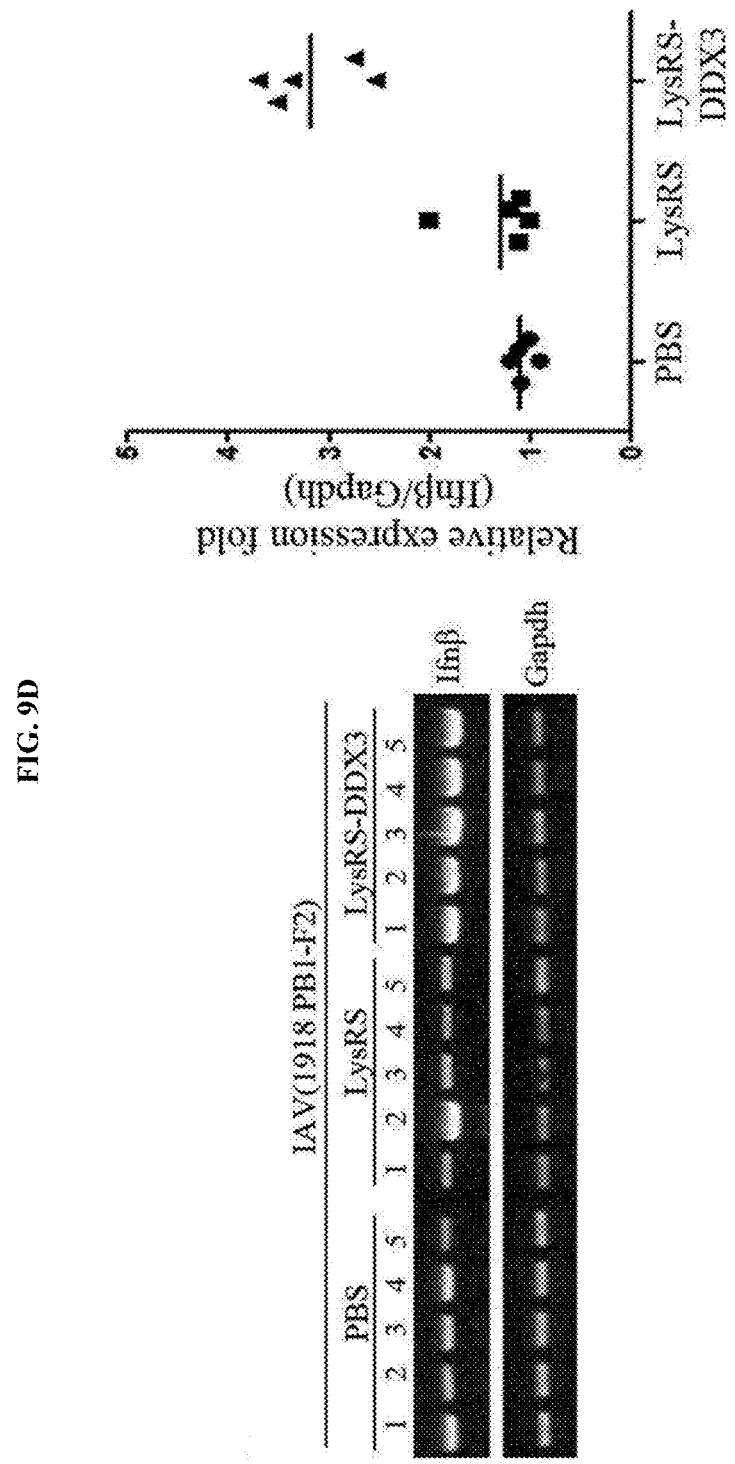

As a result, as shown in FIG. 9b, it was confirmed that all the DDX3-administered mice are alive for 2 weeks. In addition, as the result of measuring the virus titer in the mouse lung, as shown in FIG. 9c, it was confirmed that the virus titer in the DDX3 protein-administered mice was approximately 37-fold lower than those of the control groups, indicating that viral clearance occurs due to DDX3 addition. In addition, as shown in FIG. 9d, it was confirmed that intracellular IFNβ expression is increased due to expression of the DDX3 protein in mouse lung tissue.

Figure 10:
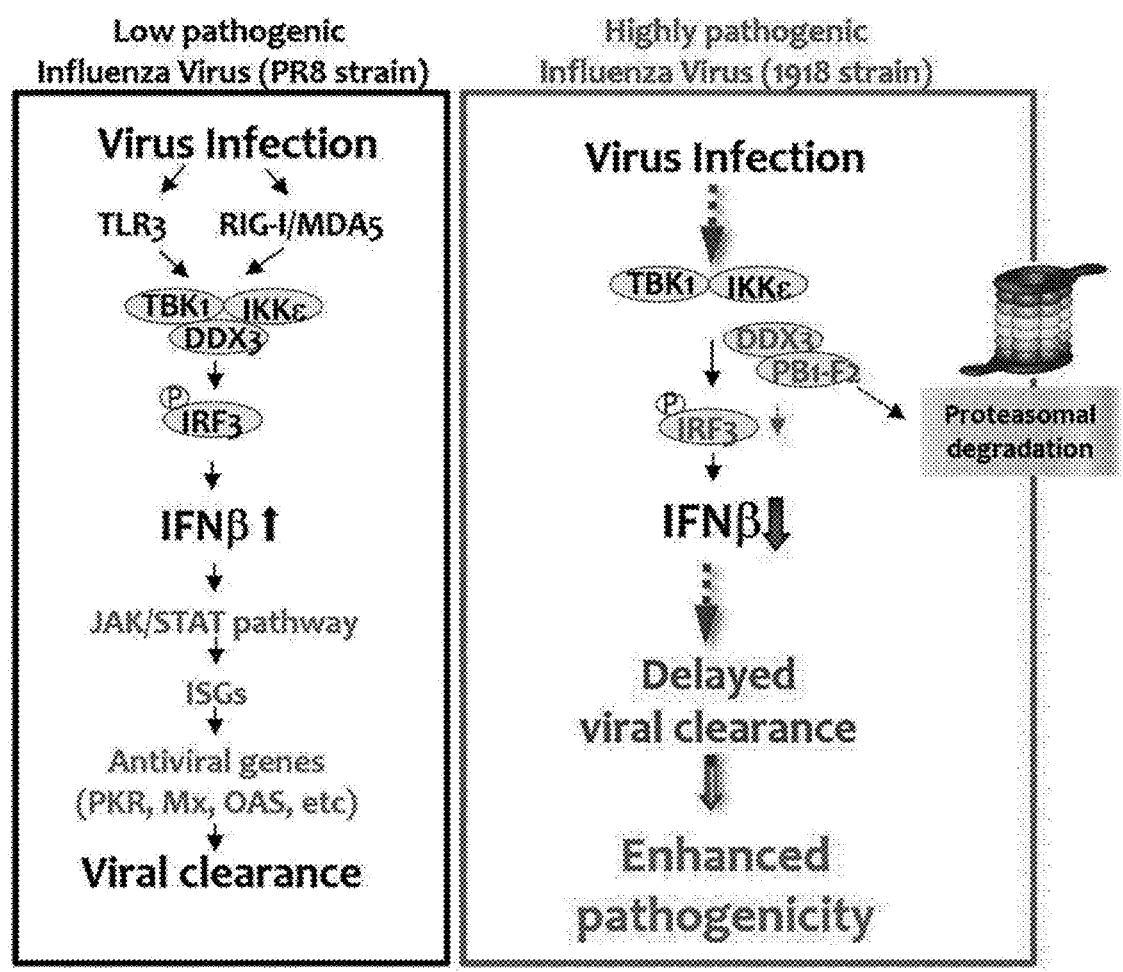
FIG. 10 illustrates the mechanism of inducing high pathogenicity through evasion of innate immunity of the 1918 strain of IAV according to the present invention.

Through the above results, it was seen that DDX3 protects the mouse from 1918 PB1-F2 viral infection. In addition, in FIG. 10, an innate immunity evasion model of the highly pathogenic 1918 strain of IAV identified by the example was illustrated.

It would be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The viral mechanism of the evasion of innate immunity by the PB1-F2 protein mutants newly identified in the present invention can provide a new understanding for developing an antiviral agent, and an antiviral composition according to the present invention can be effectively used in the development of an antiviral agent.

The invention claimed is:

1. A method for detecting a highly pathogenic virus, comprising:
measuring whether an unknown virus has a PB1-F2 protein mutant, and
determining an unknown virus measured to have the PB1-F2 protein mutant to be a highly pathogenic virus,
wherein the PB1-F2 protein mutant consists of the amino acid sequence of SEQ ID NO: 1 wherein the isoleucine and leucine at positions 68 and 69 are substituted with threonine and proline, respectively.

2. The method of claim 1, wherein the protein mutant consists of the amino acid sequence of SEQ ID NO: 2.

3. The method of claim 1, wherein the virus is an influenza virus.

4. A method for screening an antiviral substance against influenza A virus, comprising:
(a) in vitro treating cells with a candidate substance;
(b) measuring binding between DDX3 and a PB1-F2 protein in the cells;
(c) selecting a substance measured to inhibit the binding between the DDX3 and the PB1-F2 protein, compared to a group which is not treated with a candidate substance; and
(d) determining the selected substance to be an antiviral substance against influenza A virus,
wherein the PB1-F2 protein mutant consists of the amino acid sequence of SEQ ID NO: 1 wherein the isoleucine and leucine at positions 68 and 69 are substituted with threonine and proline, respectively.

5. The method of claim 4, wherein the candidate substance is selected from the group consisting of a nucleic acid, a compound, a microbial culture medium or extract, a natural substance extract, a peptide, a substrate analog, an aptamer, and an antibody.

6. The method of claim 5, wherein the nucleic acid is selected from the group consisting of siRNA, shRNA, microRNA, antisense RNA, an aptamer, a locked nucleic acid (LNA), a peptide nucleic acid (PNA), and a morpholino.

7. The method of claim 4, wherein step (b) is executed using a method selected from the group consisting of western blotting, immunoprecipitation, immunohistochemistry, and immunofluorescence.

8. The method of claim 4, wherein the PB1-F2 protein consists of the amino acid sequence of SEQ ID NO: 2.

* * * * *

SEQUENCE LISTING

```
<160> NUMBER OF SEQ ID NOS: 41

<210> SEQ ID NO 1
<211> LENGTH: 87
<212> TYPE: PRT
<213> ORGANISM: Artificial Sequence
<220> FEATURE:
<223> OTHER INFORMATION: PB1-F2

<400> SEQUENCE: 1

Met Gly Gln Glu Gln Asp Thr Pro Trp Ile Leu Ser Thr Gly His Ile
1               5                   10                  15

Ser Thr Gln Lys Arg Gln Asp Gly Gln Gln Thr Pro Lys Leu Glu His
            20                  25                  30

Arg Asn Ser Thr Arg Leu Met Gly His Cys Gln Lys Thr Met Asn Gln
        35                  40                  45

Val Val Met Pro Lys Gln Ile Val Tyr Trp Lys Gln Trp Leu Ser Leu
    50                  55                  60

Arg Asn Pro Ile Leu Val Phe Leu Lys Thr Arg Val Leu Lys Arg Trp
65                  70                  75                  80

Arg Leu Phe Ser Lys His Glu
                85

<210> SEQ ID NO 2
<211> LENGTH: 90
<212> TYPE: PRT
<213> ORGANISM: Artificial Sequence
<220> FEATURE:
<223> OTHER INFORMATION: PB1-F2 mutant

<400> SEQUENCE: 2

Met Gly Gln Glu Gln Asp Thr Pro Trp Ile Leu Ser Thr Gly His Ile
1               5                   10                  15
```

Ser Thr Gln Lys Arg Glu Asp Gly Gln Gln Thr Arg Lys Leu Glu His
            20                  25                  30

His Asn Ser Thr Arg Leu Met Asp His Cys Gln Lys Thr Met Asn Gln
        35                  40                  45

Val Val Met Pro Lys Gln Ile Val Tyr Trp Lys Gln Trp Leu Ser Leu
50                  55                  60

Arg Ser Pro Thr Pro Val Ser Leu Lys Thr Arg Val Leu Lys Arg Trp
65                  70                  75                  80

Arg Leu Phe Ser Lys His Glu Trp Thr Ser
            85                  90

<210> SEQ ID NO 3
<211> LENGTH: 612
<212> TYPE: PRT
<213> ORGANISM: Artificial Sequence
<220> FEATURE:
<223> OTHER INFORMATION: DDX3

<400> SEQUENCE: 3

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
            85                  90                  95

Asp Asp Arg Gly Arg Ser Asp Tyr Asp Gly Ile Gly Ser Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
            165                 170                 175

Pro His Ile Glu Ser Phe Ser Asp Val Glu Met Gly Glu Ile Ile Met
        180                 185                 190

Gly Asn Ile Glu Leu Thr Arg Tyr Thr Arg Pro Thr Pro Val Gln Lys
    195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
            245                 250                 255

Asn Gly Arg Tyr Gly Arg Arg Lys Gln Tyr Pro Ile Ser Leu Val Leu
        260                 265                 270

Ala Pro Thr Arg Glu Leu Ala Val Gln Ile Tyr Glu Glu Ala Arg Lys
    275                 280                 285

Phe Ser Tyr Arg Ser Arg Val Arg Pro Cys Val Val Tyr Gly Gly Ala
    290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
        355                 360                 365

Thr Met Pro Pro Lys Gly Val Arg His Thr Met Met Phe Ser Ala Thr
370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
        435                 440                 445

Glu Thr Lys Lys Gly Ala Asp Ser Leu Glu Asp Phe Leu Tyr His Glu
450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
        515                 520                 525

Ile Gly Arg Thr Gly Arg Val Gly Asn Leu Gly Leu Ala Thr Ser Phe
530                 535                 540

Phe Asn Glu Arg Asn Ile Asp Tyr Arg Gln Ser Ser Gly Ala Ser Ser
545                 550                 555                 560

Ser Ser Phe Ser Ser Arg Ala Ser Ser Arg Ser Gly Gly Gly
                565                 570                 575

Gly His Gly Ser Ser Arg Gly Phe Gly Gly Gly Tyr Gly Gly Phe
            580                 585                 590

Tyr Asn Ser Asp Gly Tyr Gly Asn Tyr Asn Ser Gln Gly Val Asp
                595                 600                 605

Trp Trp Gly Asn
    610

<210> SEQ ID NO 4
<211> LENGTH: 30
<212> TYPE: DNA
<213> ORGANISM: Artificial Sequence
<220> FEATURE:
<223> OTHER INFORMATION: PB1-F2_Forward

<400> SEQUENCE: 4
accgaattca tggactacaa ggatgacgac                                    30

<210> SEQ ID NO 5
<211> LENGTH: 27

<212> TYPE: DNA
<213> ORGANISM: Artificial Sequence
<220> FEATURE:
<223> OTHER INFORMATION: PB1-F2_Reverse

<400> SEQUENCE: 5
accctcgagc tactcgtgtt tgctgaa                                              27

<210> SEQ ID NO 6
<211> LENGTH: 27
<212> TYPE: DNA
<213> ORGANISM: Artificial Sequence
<220> FEATURE:
<223> OTHER INFORMATION: R59K_Forward

<400> SEQUENCE: 6
gtgtattgga agcgatggct ttccttg                                              27

<210> SEQ ID NO 7
<211> LENGTH: 27
<212> TYPE: DNA
<213> ORGANISM: Artificial Sequence
<220> FEATURE:
<223> OTHER INFORMATION: R59K_Reverse

<400> SEQUENCE: 7
caaggaaagc catcgcttcc aatacac                                              27

<210> SEQ ID NO 8
<211> LENGTH: 27
<212> TYPE: DNA
<213> ORGANISM: Artificial Sequence
<220> FEATURE:
<223> OTHER INFORMATION: R59K/R60Q_Forward

<400> SEQUENCE: 8
gtgtattgga ggcaatggct ttccttg                                              27

<210> SEQ ID NO 9
<211> LENGTH: 27
<212> TYPE: DNA
<213> ORGANISM: Artificial Sequence
<220> FEATURE:
<223> OTHER INFORMATION: R59K/R60Q_Reverse

<400> SEQUENCE: 9
caaggaaagc cattgcctcc aatacac                                              27

<210> SEQ ID NO 10
<211> LENGTH: 27
<212> TYPE: DNA
<213> ORGANISM: Artificial Sequence
<220> FEATURE:
<223> OTHER INFORMATION: R59K/R60Q/N66S_Forward

<400> SEQUENCE: 10
gtgtattgga agcgatggct ttccttg                                              27

<210> SEQ ID NO 11
<211> LENGTH: 27
<212> TYPE: DNA
<213> ORGANISM: Artificial Sequence
<220> FEATURE:
<223> OTHER INFORMATION: R59K/R60Q/N66S_Reverse

<400> SEQUENCE: 11
caaggaaagc catcgcttcc aatacac                                            27

<210> SEQ ID NO 12
<211> LENGTH: 24
<212> TYPE: DNA
<213> ORGANISM: Artificial Sequence
<220> FEATURE:
<223> OTHER INFORMATION: R59K/R60Q/N66S/I68T_Forward

<400> SEQUENCE: 12
ctttccttga ggaatcccac cccg                                               24

<210> SEQ ID NO 13
<211> LENGTH: 24
<212> TYPE: DNA
<213> ORGANISM: Artificial Sequence
<220> FEATURE:
<223> OTHER INFORMATION: R59K/R60Q/N66S/I68T_Reverse

<400> SEQUENCE: 13
cggggtggga ttcctcaagg aaag                                               24

<210> SEQ ID NO 14
<211> LENGTH: 27
<212> TYPE: DNA
<213> ORGANISM: Artificial Sequence
<220> FEATURE:
<223> OTHER INFORMATION: R59K/R60Q/N66S/I68T/L69P_Forward

<400> SEQUENCE: 14
cttgaggagt cccatcccgg tatcttt                                            27

<210> SEQ ID NO 15
<211> LENGTH: 27
<212> TYPE: DNA
<213> ORGANISM: Artificial Sequence
<220> FEATURE:
<223> OTHER INFORMATION: R59K/R60Q/N66S/I68T/L69P_Reverse

<400> SEQUENCE: 15
caaagatacc gggatgggac tcctcaa                                            27

<210> SEQ ID NO 16
<211> LENGTH: 27
<212> TYPE: DNA
<213> ORGANISM: Artificial Sequence
<220> FEATURE:
<223> OTHER INFORMATION: I68T_Forward

<400> SEQUENCE: 16
ttgaggaatc ccaccctggt atttttg                                            27

<210> SEQ ID NO 17
<211> LENGTH: 27
<212> TYPE: DNA
<213> ORGANISM: Artificial Sequence
<220> FEATURE:
<223> OTHER INFORMATION: I68T_Reverse

<400> SEQUENCE: 17
caaaaatacc agggtgggat tcctcaa                                            27

<210> SEQ ID NO 18
<211> LENGTH: 27
<212> TYPE: DNA
<213> ORGANISM: Artificial Sequence

```
<220> FEATURE:
<223> OTHER INFORMATION: L69P_Forward

<400> SEQUENCE: 18
aggaatccca tcccggtatt tttgaaa                                              27

<210> SEQ ID NO 19
<211> LENGTH: 27
<212> TYPE: DNA
<213> ORGANISM: Artificial Sequence
<220> FEATURE:
<223> OTHER INFORMATION: L69P_Reverse

<400> SEQUENCE: 19
tttcaaaaat accgggatgg gattcct                                              27

<210> SEQ ID NO 20
<211> LENGTH: 30
<212> TYPE: DNA
<213> ORGANISM: Artificial Sequence
<220> FEATURE:
<223> OTHER INFORMATION: I68T/L69P_Forward

<400> SEQUENCE: 20
ttgaggaatc caccccggt atttttgaaa                                            30

<210> SEQ ID NO 21
<211> LENGTH: 30
<212> TYPE: DNA
<213> ORGANISM: Artificial Sequence
<220> FEATURE:
<223> OTHER INFORMATION: I68T/L69P_Reverse

<400> SEQUENCE: 21
tttcaaaaat accggggtgg gattcctcaa                                           30

<210> SEQ ID NO 22
<211> LENGTH: 28
<212> TYPE: DNA
<213> ORGANISM: Artificial Sequence
<220> FEATURE:
<223> OTHER INFORMATION: T68I_Forward

<400> SEQUENCE: 22
cttgaggagt cccatcccgg tatctttg                                             28

<210> SEQ ID NO 23
<211> LENGTH: 27
<212> TYPE: DNA
<213> ORGANISM: Artificial Sequence
<220> FEATURE:
<223> OTHER INFORMATION: T68I_Reverse

<400> SEQUENCE: 23
caaagatacc gggatgggac tcctcaa                                              27

<210> SEQ ID NO 24
<211> LENGTH: 28
<212> TYPE: DNA
<213> ORGANISM: Artificial Sequence
<220> FEATURE:
<223> OTHER INFORMATION: P69L_Forward

<400> SEQUENCE: 24
ggagtcccac cctggtatct tgaaaac                                              28
```

```
<210> SEQ ID NO 25
<211> LENGTH: 28
<212> TYPE: DNA
<213> ORGANISM: Artificial Sequence
<220> FEATURE:
<223> OTHER INFORMATION: P69L_Reverse

<400> SEQUENCE: 25
gttttcaaag ataccagggt gggactcc                                      28

<210> SEQ ID NO 26
<211> LENGTH: 30
<212> TYPE: DNA
<213> ORGANISM: Artificial Sequence
<220> FEATURE:
<223> OTHER INFORMATION: T68I/P69L_Forward

<400> SEQUENCE: 26
ttgaggagtc ccatcctggt atctttgaaa                                    30

<210> SEQ ID NO 27
<211> LENGTH: 30
<212> TYPE: DNA
<213> ORGANISM: Artificial Sequence
<220> FEATURE:
<223> OTHER INFORMATION: T68I/P69L_Reverse

<400> SEQUENCE: 27
tttcaaagat accaggatgg gactcctcaa                                    30

<210> SEQ ID NO 28
<211> LENGTH: 20
<212> TYPE: DNA
<213> ORGANISM: Artificial Sequence
<220> FEATURE:
<223> OTHER INFORMATION: IFNb_Forward

<400> SEQUENCE: 28
gcctggcttc catcatgaac                                               20

<210> SEQ ID NO 29
<211> LENGTH: 20
<212> TYPE: DNA
<213> ORGANISM: Artificial Sequence
<220> FEATURE:
<223> OTHER INFORMATION: IFNb_Reverse

<400> SEQUENCE: 29
gaggcatcaa ctgacaggtc                                               20

<210> SEQ ID NO 30
<211> LENGTH: 24
<212> TYPE: DNA
<213> ORGANISM: Artificial Sequence
<220> FEATURE:
<223> OTHER INFORMATION: PB1-F2_Forward

<400> SEQUENCE: 30
atgggaccgg aacaggatac acca                                          24

<210> SEQ ID NO 31
<211> LENGTH: 24
<212> TYPE: DNA
<213> ORGANISM: Artificial Sequence
<220> FEATURE:
<223> OTHER INFORMATION: PB1-F2_Reverse
```

<400> SEQUENCE: 31
ctactcgtgt tgctgaaca acct                                          24

<210> SEQ ID NO 32
<211> LENGTH: 20
<212> TYPE: DNA
<213> ORGANISM: Artificial Sequence
<220> FEATURE:
<223> OTHER INFORMATION: IL-1b_Forward

<400> SEQUENCE: 32
tcaggcaggc cgcgtcagtt                                              20

<210> SEQ ID NO 33
<211> LENGTH: 21
<212> TYPE: DNA
<213> ORGANISM: Artificial Sequence
<220> FEATURE:
<223> OTHER INFORMATION: IL-1b_Reverse

<400> SEQUENCE: 33
ttgctgtgag tcccggagcg t                                            21

<210> SEQ ID NO 34
<211> LENGTH: 20
<212> TYPE: DNA
<213> ORGANISM: Artificial Sequence
<220> FEATURE:
<223> OTHER INFORMATION: IL-6_Forward

<400> SEQUENCE: 34
agcgccttcg gtccagttgc                                              20

<210> SEQ ID NO 35
<211> LENGTH: 21
<212> TYPE: DNA
<213> ORGANISM: Artificial Sequence
<220> FEATURE:
<223> OTHER INFORMATION: IL-6_Reverse

<400> SEQUENCE: 35
tgccagtgcc tctttgctgc t                                            21

<210> SEQ ID NO 36
<211> LENGTH: 20
<212> TYPE: DNA
<213> ORGANISM: Artificial Sequence
<220> FEATURE:
<223> OTHER INFORMATION: IL-32_Forward

<400> SEQUENCE: 36
gaaggcccga atggtaatgc                                              20

<210> SEQ ID NO 37
<211> LENGTH: 20
<212> TYPE: DNA
<213> ORGANISM: Artificial Sequence
<220> FEATURE:
<223> OTHER INFORMATION: IL-32_Reverse

<400> SEQUENCE: 37
tcggcaccgt aatccatctc                                              20

<210> SEQ ID NO 38

```
<211> LENGTH: 20
<212> TYPE: DNA
<213> ORGANISM: Artificial Sequence
<220> FEATURE:
<223> OTHER INFORMATION: GAPDH_Forward

<400> SEQUENCE: 38
cgtcttcacc accatggaga                                                 20

<210> SEQ ID NO 39
<211> LENGTH: 20
<212> TYPE: DNA
<213> ORGANISM: Artificial Sequence
<220> FEATURE:
<223> OTHER INFORMATION: GAPDH_Reverse

<400> SEQUENCE: 39
cggccatcac gccacagttt                                                 20

<210> SEQ ID NO 40
<211> LENGTH: 57
<212> TYPE: DNA
<213> ORGANISM: Artificial Sequence
<220> FEATURE:
<223> OTHER INFORMATION: LysRS-R9-DDX3_Forward

<400> SEQUENCE: 40
gtcacgggta cccgtcgccg tcgccgtcgc cgtcgccgta tgagtcatgt ggcagtg       57

<210> SEQ ID NO 41
<211> LENGTH: 43
<212> TYPE: DNA
<213> ORGANISM: Artificial Sequence
<220> FEATURE:
<223> OTHER INFORMATION: LysRS-R9-DDX3_Reverse

<400> SEQUENCE: 41
gtcacggtcg acgttacccc accagtcaac ccctgggag tta                       43
```